United States Patent [19]

Kane

[11] 4,239,689

[45] Dec. 16, 1980

[54] TOTAL SYNTHESIS OF THE UTERO-EVACUANT SUBSTANCE D,L-ZOAPATANOL

[75] Inventor: Vinayak V. Kane, Princeton, N.J.

[73] Assignee: Ortho Pharmaceutical Corporation, Raritan, N.J.

[21] Appl. No.: 970,727

[22] Filed: Dec. 18, 1978

[51] Int. Cl.$^3$ ............................................ C07D 313/04
[52] U.S. Cl. ............................... 260/333; 260/348.54; 260/340.9 R; 260/345.9 R
[58] Field of Search .......................................... 260/333

[56] References Cited

U.S. PATENT DOCUMENTS

| | | | |
|---|---|---|---|
| 4,060,604 | 11/1977 | Kanojia | 424/278 |
| 4,086,358 | 4/1978 | Wachter et al. | 424/278 |
| 4,112,078 | 9/1978 | Chen | 424/278 |

Primary Examiner—Norma S. Milestone
Attorney, Agent, or Firm—Benjamin F. Lambert

[57] ABSTRACT

A method for the synthesis of racemic 2S*, 3R*-6E-(2''-hydroxyethylidene)-2-methyl-2-(4',8'-dimethyl-5'-oxo-7'-nonenyl)-oxepan-3-ol is described. The naturally occurring product, 2S, 3R-6E-(2''-hydroxyethylidene)-2-methyl-2-(4',8'-dimethyl-5'-oxo-7'-nonenyl)-oxepan-3-ol, is one of the active components of the zoapatle plant.

4 Claims, No Drawings

TOTAL SYNTHESIS OF THE UTERO-EVACUANT SUBSTANCE D,L-ZOAPATANOL

The zoapatle plant is a bush about two meters high that grows wild in Mexico. Botanically, it is known as *Montanoa tomentosa* according to Cervantes, Fam. *Compositae*, Tribe *Heliantheae;* another variety of the species is *Montanoa floribunda*. The plant is described in great detail in *Las Plantas Medicinales de Mexico*, Third Edition, Ediciones Botas (1944).

The plant has been used for centuries in the form of a "tea" or other crude aqueous preparations primarily as a labor inducer or menses inducer for women. Its use as a utero-evacuant has been documented in the literature.

In U.S. Pat. No. 4,086,358, a method is described for the isolation of the active ingredients in the zoapatle plant. One of the active ingredients is 2S, 3R-6E-(2-hydroxyethylidene)-2-methyl-2-(4',8'-dimethyl-5'-oxo-7'-nonenyl)-oxepan-3-ol. This compound, referred to as zoapatanol, has the following structural formula:

The present invention relates to a method for the total synthesis of 2S*, 3R*-6E-(2-hydroxyethylidene)-2-methyl-2-(4',8'-dimethyl-5'-oxo-7'-nonenyl)-oxepan-3-ol and 2S*, 3R*-6Z-(2-hydroxyethylidene)-2-methyl-2-(4',8'-dimethyl-5'-oxo-7'-nonenyl)-oxepan-3-ol.

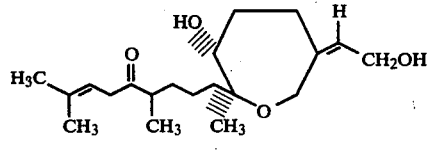

The asterisk in the name (e.g. 2S*, 3R*-) indicates the racemic nature of the compound and refers thus to the relative configuration of the chiral centers. The lettering of the appropriate positions corresponds to that of the naturally occurring optical isomer 21 (e.g. 2S, 3R).

Many of the intermediates employed in the synthesis of zoapatanol are novel compounds and are included as part of the invention.

The synthesis is comprised of several steps which are summarized in the following schematic diagram:

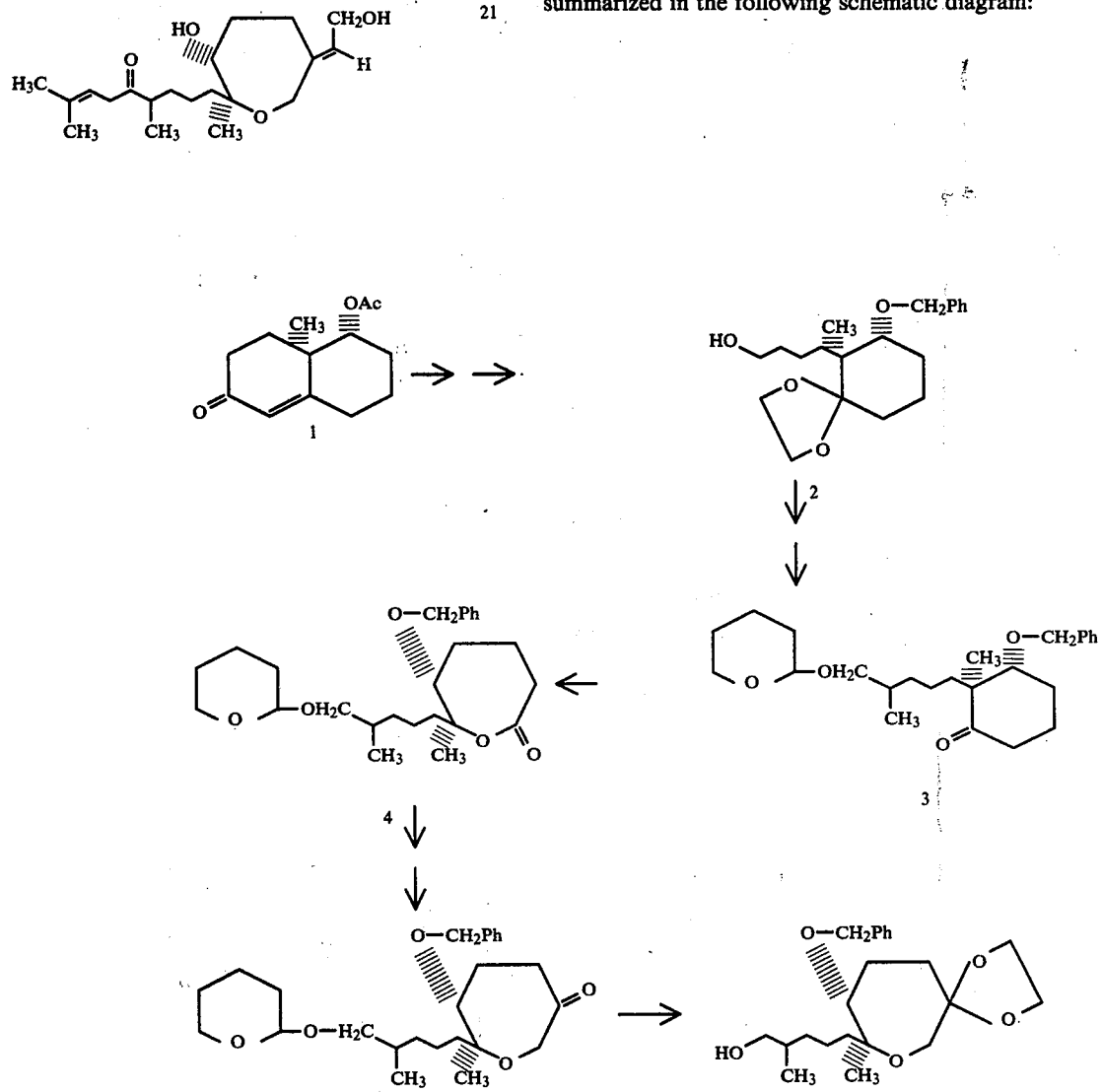

-continued
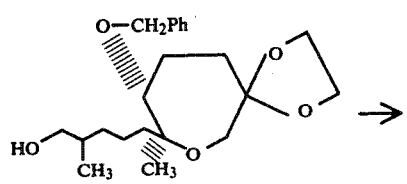
6
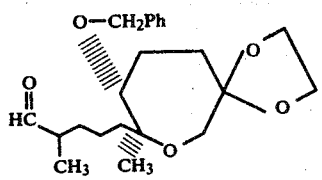
7
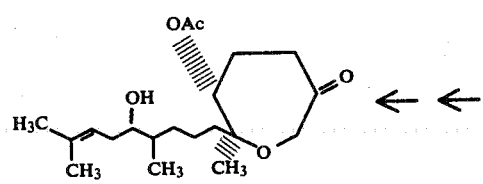
9
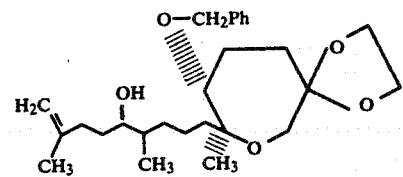
8
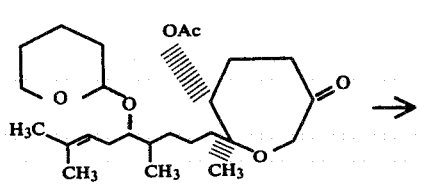
10
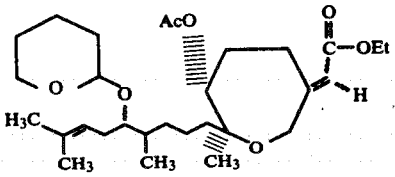
11
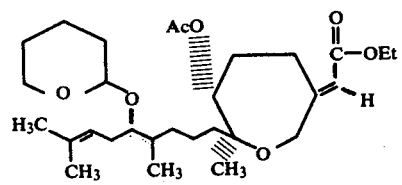
11
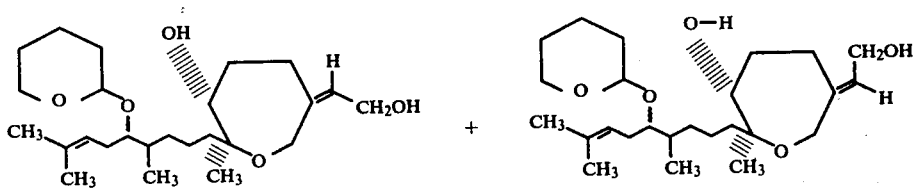
12        17

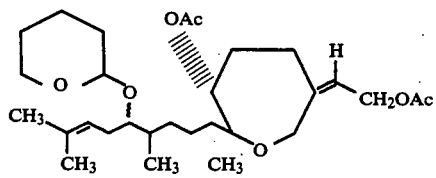

13

-continued

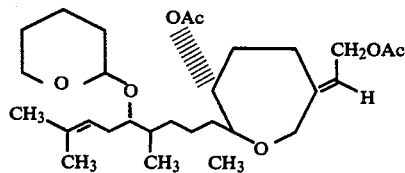

18

↓

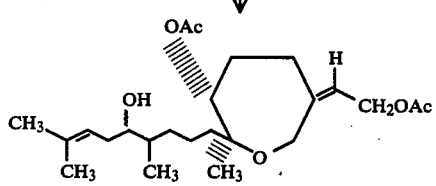

14

↓

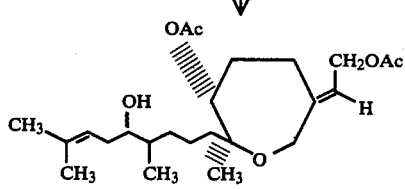

19

↓

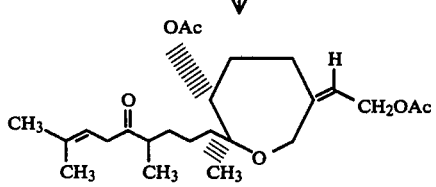

15

↓

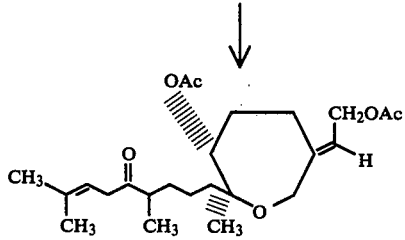

20

↓

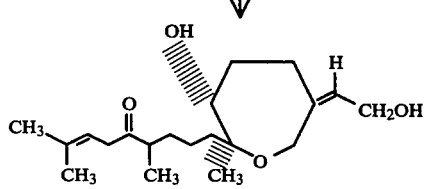

16

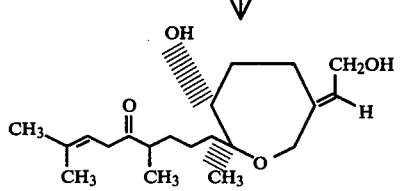

21

In the above diagram, the symbols Ph, Ac and Et refer to phenyl, acetyl and ethyl groups, respectively.

As seen from the diagram, the first series of steps in the synthesis involves the preparation of a compound (2) having 11 of the carbon atoms in zoapatanol. The compound (2) is prepared from the ketone (1) in eight steps. In the first step, the ketone (1) is converted to the corresponding ethylenedioxy derivative by reaction with ethylene glycol. The reaction is preferably carried out in the presence of a catalyst such as, for example, p-toluenesulfonic acid, camphorsulfonic acid and oxalic acid in a suitable solvent such as benzene or toluene. Solvents which can be employed include benzene, toluene and the xylenes. The reaction is carried out at elevated temperatures, preferably at the reflux temperature of the solvent. The product is separated from the reaction mixture by techniques known to those skilled in the art. The acetate is then converted to the free hydroxy compound by reaction with a mild alkali such as sodium carbonate or potassium carbonate in a suitable solvent. Solvents which can be employed include alcohols such as methanol and ethanol. The product is removed from the reaction mixture by techniques known to those skilled in the art. The third step involves the reprotection of the hydroxyl group present in the ketal-alcohol. Suitable protecting groups which can be employed include benzyl, p-nitrobenzyl and p-methylbenzyl. The protecting group is preferably added in the form of a halide. Suitable halides which can be employed include benzyl bromide, benzyl iodide and benzyl chloride. The reaction product is then separated from the mixture by techniques known to those skilled in the art.

The ethylenedioxy-octalin compound having the protective group on the hydroxyl oxygen is then converted to the free ketone by reaction with an aqueous acid such as aqueous sulfuric acid, or camphorsulfonic acid, or p-toluenesulfonic acid in a suitable solvent mixture such as water-acetone, or with an organic acid such as, for example, acetic acid in a solvent such as methanol. The resulting ketone is then converted to the corresponding 5 (10) oxido compound by reaction with a peroxide such as hydrogen peroxide, for example, in the presence of a base such as sodium hydroxide or potassium hydroxide. The reaction is preferably carried out at a temperature between about 0° C. and room temperature; the preferred reaction temperature is between about 0° C. and 5° C. The ring containing the keto group in the 5 (10) oxido compound is then opened to give a four carbon side chain having a terminal triple bond. This is accomplished by reacting the 5 (10) oxido compound with p-toluenesulfonylhydrazide or 2,4-dinitro p-toluenesulfonylhydrazide in a suitable solvent such as methylene chloride. The reaction is preferably carried out at a temperature betwen 0° C. and 25° C. The product, (2S*, 3R*)-3-benzyloxy-2-(3'-butynyl)-2-methylcyclohexanone, is separated from the reaction mixture by methods known to those skilled in the art. The methylcyclohexanone compound is then converted to the corresponding ketal by reaction with ethylene glycol in the presence of a catalyst such as p-toluenesulfonic acid as described above. The triple bond in the side chain is converted to a primary alcohol by reaction with 9-borabicyclononane or with thexylmonoalkyl boranes in a suitable solvent such as tetrahydrofuran or diglyme, for example, followed by reaction with a peroxide such as hydrogen peroxide in the presence of a base such as aqueous sodium hydroxide or potassium hydroxide. The reactions can be carried out at a temperature between about 0° C. and room temperature; the preferred reation temperature is between about 0° C. and 5° C. The product, (2S*, 3R*)-3-benzyloxy-1,1-ethylenedioxy-2-(4'-hydroxybutyl)-2-methylcyclohexane (2) is separated from the reaction mixture by methods known to those skilled in the art. In a preferred method the compound (2) is purified by chromatography on SilicAR CC-7 in a suitable solvent such as hexane, petroleum ether 40/60° or pentane, for example. The purified material is obtained by eluting the column with ethyl acetate/hexane.

The ketone intermediate (2S*, 3R*)-3-benzyloxy-2-methyl-2-[4'-methyl-5'-(tetrahydropyran-2"-yloxy)-pentyl]-cyclohexanone (3) is synthesized from (2S*, 3R*)-3-benzyloxy-1,1-ethylenedioxy-2-(4'-hydroxybutyl)-2-methylcyclohexane (2) via a seven step sequence. The first step in the synthesis is the oxidation of the alcohol (2) to the corresponding aldehyde. The oxidation step is carried out with a suitable oxidizing agent such as, for example, chromium trioxide in pyridine in a suitable solvent such as methylene chloride. The aldehyde is then converted to the corresponding secondary alcohol by reaction with methyl lithium or methylmagnesium bromide in a suitable solvent such as ether or tetrahydrofuran, for example. The reaction is generally carried out at a temperature between 0° C. and room temperature. Reaction of the alcohol with an appropriate oxidizing agent such as chromium trioxide in pyridine in a suitable solvent such as methylene chloride gives the corresponding ketone. Reaction of the ketone with a mixture of sodium hydride and methyltriphenylphosphonium iodide or methyltriphenylphosphonium bromide in dimethylsulfoxide converts the keto group to a methylene group. Reaction of the latter compound with 9-borabicyclononane in a suitable solvent such as tetrahydrofuran or diglyme followed by reaction with a peroxide such as hydrogen peroxide in the presence of a base such as aqueous sodium hydroxide or potassium hydroxide, for example, results in the formation of a primary alcohol on the carbon side chain. The ethylene-dioxy group is then converted to a keto group by reaction with an aqueous acid such as aqueous sulfuric acid, camphorsulfonic acid or p-toluenesulfonic acid, for example, in a suitable solvent such as acetone, organic acid such as acetic acid in a solvent such as methanol. Reaction of the keto-alcohol with dihydropyran in a suitable solvent such as ether or methylene chloride results in the formation of the intermediate compound (2S*, 3R*)-3-benzyloxy-2-methyl-2-[4'-methyl-5'-(tetrahydropyran-2"-yloxy)-pentyl]-cyclohexanone (3). The cyclohexanone intermediate (3) is then converted to the lactone (4) which in turn is converted in five steps to a β-keto ether (5). The conversion to the lactone (4) is accomplished by reacting the cyclohexanone intermediate (3) with a peroxy acid such as, for example, m-chloroperoxybenzoic acid and p-nitroperoxybenzoic acid or peracetic acid in a suitable solvent such as methylene chloride or dichloroethane. The resulting lactone (4) is separated from the reaction mixture by methods known to those skilled in the art.

The first steps in the preparation of the β-keto ether (5) involve reaction of the lactone (4) first with lithium diisopropylamide and then with diethylchlorophosphate in a suitable solvent such as tetrahydrofuran. The reaction is preferably carried out at a temperature between about −78° and 0° C. in the presence of tetramethylethylenediamine, for example. The resulting 6,7-unsaturated diethyl oxepinyl phosphate compound is then reacted with sodium in liquid ammonia to remove the phosphate and the benzyl protecting groups. The hydroxyl group is reprotected by reaction of the oxepene compound with a benzyl halide in the presence of a base such as sodium hydride or potassium hydride. Reaction of the benzyloxy-6-oxepene compound with diborane followed by reaction with hydrogen peroxide and aqueous sodium hydroxide or potassium hydroxide results in the addition of a hydroxyl group at the 6 position. Oxidation of the mixture of alcohols with a suitable oxidizing agent such as chromium trioxide/pyridine yields the β-keto ether intermediate (2S*, 3R*)-3-benzyloxy-2-methyl-2-[4'-methyl-5'-(tetrahydropyran-2"-yloxy)-pentyl]-oxepan-6-one (5).

The intermediate compound (2S*, 3R*)-3-benzyloxy-6,6-ethylenedioxy-2-methyl-2-(4'-methyl-5'-hydroxypentyl)-oxepane (6) is prepared from the β-keto ether (5) by reaction with ethylene glycol in the presence of a catalyst such as p-toluenesulfonic acid, for example, in a suitable solvent such as benzene.

The aldehyde (7) is prepared from the ketal (6) by oxidation with a suitable oxidizing agent such as, for example, chromium trioxide/pyridine. The aldehyde (7) is then reacted with the Grignard reagent generated from 4-bromo-2-methyl-1-butene to give (2S*, 3R*)-3-benzyloxy-6,6-ethylenedioxy-2-methyl-2-(4',8'-dimethyl-5'-hydroxy-8'-nonenyl)-oxepane (8) which has the side chain length present in zoapatanol.

The β-keto ether intermediate (2S*, 3R*)-3-acetoxy-2-methyl-2-(4',8'-dimethyl-5'-hydroxy-7'-nonenyl)-oxepan-6-one (9) is prepared from the ketal (8) in seven steps. In the first step, compound (8) is converted to the corresponding lower alkyl ester by reaction with a lower alkyl anhydride such as, for example, acetic anhydride, propionic anhydride, butyric anhydride and acyl halides such as acetyl chloride, propionyl bromide or propionyl chloride under the usual conditions for esterification. The 8'-nonenyl-oxepane ester is then converted to the 7'-nonenyl-oxepane ester by reaction with p-toluenesulfonic acid in a suitable solvent such as benzene or toluene. It is preferred to use an anhydrous solvent. The 7'-nonenyl-oxepane ester is then hydrolyzed to the 5'-alcohol with a mild base such as potassium carbonate or sodium carbonate in a suitable solvent such as methanol or a mixture of methanol and water. The 5'-alcohol is then converted to the tetrahydropyranyl derivative by reaction with dihydropyran in a suitable solvent such as ether or methylene chloride. The reaction is preferably carried out in the presence of an acid such as p-toluenesulfonic acid or camphorsulfonic acid. The benzyl protecting group is removed by reacting the tetrahydropyranyl derivative with sodium in liquid ammonia and t-butanol. The resulting hydroxy ketal is then esterified with an esterifying agent such as a lower alkyl anhydride or a lower alkanoyl halide. Esterifying agents which can be employed include acetic anhydride, propionic anhydride, butyric anhydride and acyl halides such as acetyl chloride, propionyl bromide and propionyl chloride in the presence of a base such as pyridine. Acid hydrolysis of the tetrahydropyranyl ketal gives the β-keto ether (2S*, 3R*)-3-acetoxy-2-methyl-2-(4',8'-dimethyl-5'-hydroxy-7'-nonenyl)-oxepan-6-one (9).

The β-keto ether (9) is then converted to its tetrahydropyranyl derivative (10) by reaction with dihydropyran as described above. The tetrahydropyranyl derivative is then converted to its carboethoxymethylidene derivative (11) by reaction with triethyl phosphonoacetate in the presence of a base such as sodium hydride. The product is separated from the reaction mixture by methods known to those skilled in the art. Reduction of the carboethoxymethylidene derivative (11) with lithium aluminum hydride in a suitable solvent such as ether, tetrahydrofuran and dimethoxyethane, for example, gives a mixture of diols (12 and 17).

The diols are separated by methods known to those skilled in the art. Column chromatography on an adsorbent material such as silica gel is a preferred method. The diols (12,Z isomer and 17,E isomer) each contain all of the 20 carbon atoms present in zoapatanol (E-isomer). A four step sequence converts the diols (12 and 17) to racemic zoapatanol (21) and to the racemic isomer (16).

The first step in the synthesis of the naturally occurring isomer (21) from the diol (17) involves the preparation of the corresponding diester (18). The diester (18) is prepared by conventional means from a lower alkyl anhydride or acyl halide such as, for example, acetic anhydride or acetyl chloride in the presence of a base such as pyridine. The tetrahydropyranyl protecting group is removed by treating the diester (18) with an organic acid such as acetic acid, p-toluenesulfonic acid or camphorsulfonic acid in a suitable solvent such as tetrahydrofuran, for example. The alcohol (19) which forms is then oxidized to the corresponding ketone (20) with an oxidizing agent such as chromium trioxide/pyridine. Reaction of the ketone (20) with tetrabutylammonium hydroxide in a suitable solvent such as methanol yields racemic zoapatanol. The same series of reactions when carried out on the isomeric diol (12) leads to the Z isomer (16).

As used herein, the term lower alkyl means an alkyl group having from 1–5 carbon atoms and the term lower alkanoyl means an alkanoyl group having from 2–5 carbon atoms.

The following describes the invention in greater particularity and is intended to be a way of illustrating but not limiting the invention.

EXAMPLE 1

(1R*, 9R*)-1-Acetoxy-6,6-ethylenedioxy-9-methyl-4(10)-octalin

A mixture of (1R*, 9R*)-1-acetoxy-9-methyl-5(10)-octalin-6-one (23 g, 0.103 mol), ethylene glycol (100 ml) and p-toluenesulfonic acid (100 mg) in benzene (700 ml) is refluxed for 16 hours using a Dean-Stark apparatus. The cooled solution is diluted with water (500 ml) and ether (500 ml). The organic layer is separated and the aqueous layer is extracted with ether (2×250 ml). The combined organic layers are washed with saturated sodium bicarbonate (4×200 ml), water (2×200 ml) and saturated sodium chloride, and dried (MgSO$_4$). The solvents are removed at reduced pressure and the crude product (26 g) is chromatographed on SilicAR CC-7 (350 g, Mallinckrodt) in hexane. Elution with 7–10% ethyl acetate/hexane gives (1R*, 9R*)-1-acetoxy-6,6-ethylenedioxy-9-methyl-4(10)-octalin as a colorless oil (22 g, 80%): ir (neat) 1724 cm$^{-1}$ (OAc); nmr (CDCl$_3$)δ 1.18 (s, 3H, C$\underline{H}_3$), 2.02 (s, 3H, —OCO—CH$_3$), 3.98 (s, 4H, ketal), 4.82 (m, 1H, —C$\underline{H}$—OAc), 5.35 (m, 1H, —C=C$\underline{H}$—).

EXAMPLE 2

(1R*, 9R*)-6,6-Ethylenedioxy-1-hydroxy-9-methyl-4(10)-octalin

A solution of (1R*, 9R*)-1-acetoxy-6,6-ethylenedioxy-9-methyl-4(10)-octalin (22 g, 0.0827 mol) and saturated potassium carbonate (100 ml) in methanol (800 ml) and water (100 ml) at 25° C. in a nitrogen atmosphere is stirred for 48 hours. The methanol is evaporated under reduced pressure, diluted with water (500 ml) and the aqueous layer is extracted with chloroform (2×700 ml). The combined organic layers are washed with water (3×600 ml) and saturated sodium chloride (3×700 ml), dried (MgSO$_4$) and evaporated in vacuo. The crude product (19 g) is chromatographed on SilicAR CC-7 (234 g, Mallinckrodt) in hexane. Elution with 20% ethyl acetate/hexane gives (1R*, 9R*)-6,6-ethylenedioxy-1-hydroxy-9-methyl-4(10)-octalin as a colorless oil (16.6 g, 87%): ir (KBr) 3546 cm$^{-1}$ (OH); nmr (CDCl$_3$)δ 1.10 (s, 3H, C$\underline{H}_3$), 3.60 (m, 1H, —CH$_2$—C$\underline{H}$—OH), 3.98 (s, 4H, ketal), 5.27 (m, 1H, —C=C$\underline{H}$—CH$_2$—).

EXAMPLE 3

(1R*, 9R*)-1-Benzyloxy-6,6-ethylenedioxy-9-methyl-4(10)-octalin

To a suspension of sodium hydride (18.7 g, 0.780 mol, 50% dispersion in oil, previously washed with hexane) in benzene (1200 ml) is added the alcohol (1R*, 9R*)-6,6-ethylenedioxy-1-hydroxy-9-methyl-4(10)-octalin (87.37 g, 0.390 mol) in benzene (100 ml) in a nitrogen atmosphere. After 0.5 hours, benzylbromide (115.0 g, 0.672 mol) in benzene (100 ml) is added. The mixture is refluxed for 24 hours, cooled and poured into saturated sodium chloride (1000 ml). The aqueous layer is extracted with diethyl ether (3×250 ml). The organic phases are combined, dried (MgSO$_4$) and the solvents are removed under reduced pressure. The crude product (137.1 g) is chromatographed on SilicAR CC-7 (550 g, Mallinckrodt) in hexane. Elution with 5–10% ethyl acetate/hexane gives (1R*, 9R*)-1-benzyloxy-6,6-ethylenedioxy-9-methyl-4(10)-octalin as a clear colorless oil (111.7 g, 91%): nmr (CDCl$_3$)δ 1.20 (s, 3H, CH$_3$), 3.36 (m, 1H, —CH—OCH$_2$Ph), 3.98 (s, 4H, ketal), 4.56 (d of d, J=10 Hz, 2H, Ph—CH$_2$—O—), 5.23 (broad s, 1H, —C=CH—CH$_2$—), 7.23 (s, 5H, aromatic).

EXAMPLE 4

(1R*, 9R*)-1-Benzyloxy-9-methyl-5(10)-octalin-6-one

A mixture of (1R*, 9R*)-1-benzyloxy-6,6-ethylenedioxy-9-methyl-4(10)-octalin (111.7 g, 0.355 mol), methanol (400 ml) and acetic acid (400 ml) is refluxed for 18 hours under a nitrogen atmosphere. The reaction mixture is cooled and the methanol and acetic acid evaporated under reduced pressure. The mixture is diluted with water (800 ml) and the aqueous layer extracted with ether (3×1000 ml). The combined organic layers are washed with saturated sodium bicarbonate, water and saturated sodium chloride and dried (MgSO$_4$). The solvents are removed under reduced pressure and the crude product (94.2 g) is chromatographed on SilicAR CC-7 (900 g., Mallinckrodt) in hexane. Elution with 10% ethyl acetate/hexane gives (1R*, 9R*)-1-benzyloxy-9-methyl-5(10)-octalin-6-one as a colorless oil (85.4 g, 89%): ir (neat) 1660, 1612 cm$^{-1}$ (α,β-unsaturated CO): nmr (CDCl$_3$)δ1.22 (s, 3H, CH$_3$), 3.16 (m, 1H, —CH—OCH$_2$Ph), 4.56 (d of d, J=10 Hz, 2H, Ph—CH$_2$—O—), 5.78 (broad s, 1H, >C—CH=CO—), 7.30 (s, 5H, aromatic).

EXAMPLE 5

(1R*, 9R*)-1-Benzyloxy-9-methyl-5(10)oxido-octalin-6-one

To a solution of (1R*, 9R*)-1-benzyloxy-9-methyl-5(10)-octalin-6-one (81.2 g, 0.300 mol) in methanol (600 g) cooled to 0° C. under nitrogen is added with stirring 30% hydrogen peroxide (136 g, 1.2 mol). While maintaining the temperature at 0° C., 6N sodium hydroxide (30 ml) is added dropwise over 20 minutes. After the addition is complete, the reaction mixture is stirred for 4 hours at 25° C. The reaction mixture is then poured into saturated sodium chloride (2000 ml) and extracted with diethyl ether (7×1000 ml). The combined organic layers are washed with water and dried (MgSO$_4$). The solvents are removed under reduced pressure to give a mixture of epoxides (1R*, 9R*)-1-benzyloxy-9-methyl-5(10)oxido-octalin-6-one (60 g, 70%): ir (neat) 1724 cm$^{-1}$ (CO); nmr (CDCl$_3$)δ1.08 (s, 3H, CH$_3$), 1.18 (s, 3H, CH$_3$), 2.82 (s, 1H, —CO—CH—CO—), 3.00 (s, 1H, —CO—CH—CO—), 4.4 (d of d, J=10 Hz, 2H, Ph—CH$_2$O—), 7.20 (s, 5H, aromatic).

EXAMPLE 6

(2S*, 3R*)-3-Benzyloxy-2-(3'-butynyl)-2-methylcyclohexanone

To a stirred solution of (1R*, 9R*)-1-benzyloxy-9-methyl-5(10)oxido-octalin-6-one (27.8 g, 0.0965 mol) in methylene chloride (500 ml) and acetic acid (350 ml) at 0° C. under nitrogen is added p-toluenesulfonylhydrazide (18.2 g, 0.097 mol) in one portion. Stirring is continued at 0° C. for 3 hours followed by 19 hours at 25° C. The reaction mixture is poured into water (1000 ml) and the methylene chloride layer is separated. The aqueous layer is extracted with methylene chloride (2×500 ml). The combined organic layers are washed with water, saturated sodium bicarbonate (2×750 ml), water, saturated sodium chloride and dried (MgSO$_4$). The solvents are removed at reduced pressure to give a slightly yellow oil (27.5 g, 100%). The crude product is chromatographed on SilicAR CC-7 (600 g, Mallinckrodt) in hexane. Elution with 10% ethyl acetate/hexane gives (2S*, 3R*)-3-benzyloxy-2-(3'-butynyl)-2-methylcyclohexanone: ir (neat) 2132 (C≡C), 1704 cm$^{-1}$, (CO); nmr (CDCl$_3$)δ1.20 (s, 3H, CH$_3$), 2.38 (m, 1H, —C≡CH), 3.50 (m, 1H, —CH—OCH$_2$Ph), 4.56 (d of d, J=10 Hz, 2H, Ph—CH$_2$—O—), 7.25 (s, 5H, aromatic).

EXAMPLE 7

(2S*, 3R*)-3-Benzyloxy-2-(3'-butynyl)-1,1-ethylenedioxy-2-methylcyclohexane

A mixture of (2S*, 3R*)-3-benzyloxy-2-(3'-butynyl)-2-methylcyclohexanone (27.5 g, 0.102 mol), ethylene glycol (100 ml) and p-toluenesulfonic acid (1 g) in benzene (600 ml) is refluxed for 20 hours using a Dean-Stark apparatus. The cooled solution is washed with saturated sodium bicarbonate (3×250 ml) and water (2×250 ml) and dried (MgSO$_4$). The solvent is removed at reduced pressure and the crude product (30.3 g) is chromatographed on SilicAR CC-7 (600 g, Mallinckrodt) in hexane. Elution with 3% ethyl acetate/hexane gives (2S*, 3R*)-3-benzyloxy-2-(3'-butynyl)-1,1-ethylenedioxy-2-methylcyclohexane as a colorless oil (23.9 g, 75%): ir (neat) 2126 cm$^{-1}$ (C≡C); nmr (CDCl$_3$)δ1.06 (s, 3H, CH$_3$), 2.30 (m, 1H, —C≡CH), 3.41 (m, 1H, —CH—OCH$_2$Ph), 3.98 (s, 4H, ketal), 4.50 (d of d, J=10 Hz, 2H, Ph—CH$_2$—O—), 7.20 (s, 5H, aromatic).

EXAMPLE 8

(2S*, 3R*)-3-Benzyloxy-1,1-ethylenedioxy-2-(4'-hydroxybutyl)-2-methylcyclohexane To a stirred solution of 9-borabicyclononane (37.1 g, 0.304 mol) in dry tetrahydrofuran (1200 ml) maintained at 0° C. in a nitrogen atmosphere is added a solution of (2S*, 3R*)-3-benzyloxy-2-(3'-butynyl)-1,1-ethylenedioxy-2-methylcyclohexane (45.2 g, 0.144 mol) in dry tetrahydrofuran (300 ml). After the addition is complete, the mixture is stirred for 5 hours at 25° C. At the end of this period, the reaction mixture is cooled to 0° C. and 3N sodium hydroxide (140 ml, 0.42 mol) followed by 30% hydrogen peroxide (159.6 g, 1.4 mol) are added while maintaining the temperature at 0° C. After the addition is complete, the mixture is stirred for 1 hour at 25° C. The mixture is then diluted with saturated sodium chloride (2000 ml) and extracted with ether (6×100 ml). The ether phases are combined, dried (MgSO$_4$) and the solvents are removed under reduced pressure. The crude product (101.9 g) is chromatographed on SilicAR CC-7 (1000 g, Mallinckrodt) in hexane. Elution with 25% ethyl acetate/hexane gives (2S*, 3R*)-3-benzyloxy-1,1-ethylenedioxy-2-(4'-hydroxybutyl)-2-methylcyclohexane as a colorless oil (42.3 g, 88%): ir (neat) 3448 cm$^{-1}$ (OH), nmr (CDCl$_3$)δ1.02 (s, 3H, C<u>H</u>$_3$), 3.92 (s, 4H, ketal), 4.50 (d of d, J=10 Hz, 2H, —O—C<u>H</u>$_2$Ph), 7.26 (s, 5H, aromatic).

EXAMPLE 9

(2S*, 3R*)-3-Benzyloxy-1,1-ethylenedioxy-2-methyl-2-(4'-oxobutyl)-cyclohexane

A pyridine-chromium trioxide solution [C$_5$H$_5$N (120 g, 1.524 mol) and CrO$_3$ (76.2 g, 0.762 mol)] is prepared in dry methylene chloride (2700 ml) at 0° C. in a nitrogen atmosphere. The cooling bath is removed and celite (300 g) is added at 15° C. At 23° C., the alcohol (2S*, 3R*)-3-benzyloxy-1,1-ethylenedioxy)-2-(4'-hydroxybutyl)-2-methylcyclohexane (42.3 g, 0.127 mol) in methylene chloride (300 ml) is added. After 1 hour, the mixture is filtered and the celite cake is washed with methylene chloride (10×100 ml) and the solvent is removed at reduced pressure. The residue is diluted with ether (750 ml) and filtered. The solvent is removed at reduced pressure and the resulting crude product (46.0 g) is chromatographed on SilicAR CC-7 (1000 g, Mallinckrodt) in hexane. Elution with 25% ethyl acetate/hexane gives (2S*, 3R*)-3-benzyloxy-1,1-ethylenedioxy-2-methyl-2-(4'-oxobutyl)-cyclohexane as a colorless oil (25.4 g, 60%): ir (neat) 1718 cm$^{-1}$ (CHO); nmr (CDCl$_3$)δ1.02 (s, 3H, C<u>H</u>$_3$), 3.90 (s, 4H, ketal), 4.46 (d of d, J=10 Hz, 2H, —O—CH$_2$Ph), 7.23 (s, 5H, aromatic), 9.63 (t, 1H, C<u>H</u>O).

EXAMPLE 10

(2S*, 3R*)-3-Benzyloxy-1,1-ethylenedioxy-2-methyl-2-(4'-hydroxypentyl)-cyclohexane Methyllithium (63.3 ml, 0.0918 mol, 1.45 M in ether) is added dropwise to a solution of the aldehyde (2S*, 3R*)-3-benzyloxy-1,1-ethylenedioxy-2-methyl-2-(4'-oxobutyl)-cyclohexane (25.4 g, 0.0765 mol) in ether (1000 ml) at 0° C. in a nitrogen atmosphere. The cooling bath is removed and the mixture is stirred for 0.5 hours at ambient temperature. The mixture is then poured into a cold saturated sodium chloride solution (500 ml). The ether phase is separated and the aqueous phase is extracted with ether (3×100 ml). The ether phases are combined, dried (MgSO$_4$) and the solvent is removed at reduced pressure. The crude product (27.1 g) is chromatographed on SilicAR CC-7 (300 g, Millinckrodt) in hexane. Elution with 10% ethyl acetate/hexane gives (2S*, 3R*)-3-benzyloxy-1,1-ethylenedioxy-2-methyl-2-(4'-hydroxypentyl)-cyclohexane as a colorless oil (25.8 g, 97%).

EXAMPLE 11

(2S*, 3R*)-3-Benzyloxy-1,1-ethylenedioxy-2-methyl-2-(4'-oxopentyl)-cyclohexane

A solution of pyridine (70.3 g, 0.89 mol) and chromium trioxide (44.5 g, 0.445 mol) in methylene chloride (1.8 l) in a nitrogen atmosphere is stirred for 45 minutes. Celite (180 g) is added followed by (2S*, 3R*)-3-benzyloxy-1,1-ethylenedioxy-2-methyl-2-(4'-hydroxypentyl)-cyclohexane (25.8 g, 0.074 mol) in methylene chloride (100 ml). The mixture is stirred for 90 minutes at 23° C. The mixture is then filtered and the celite cake is washed with methylene chloride (10×200 ml). The filtrate and washings are combined and the solvents are removed under reduced pressure to give a dark oil, which is diluted with ether (750 ml) and filtered. The ether phase is dried (MgSO$_4$) and the solvents are removed at reduced pressure. The crude product (21 g) is chromatographed on SilicAR CC-7 (300 g, Mallinckrodt) in hexane. Elution with 6% ethyl acetate/hexane gives (2S*, 3R*)-3-benzyloxy-1,1-ethylenedioxy-2-methyl-2-(4'-oxopentyl)-cyclohexane as a clear colorless oil (15.7 g, 61%): ir (neat) 1712 cm$^{-1}$ (CO); nmr (CDCl$_3$)δ 1.06 (s, 3H, CH$_3$), 2.04 (s, 3H,

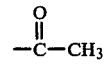

2.30 (m, 2H, —CH$_2$—CO), 3.50 (m, 1H, —CH—OCH$_2$Ph), 3.98 (s, 4H, ketal), 4.55 (d of d, J=10 Hz, 2H, —O—CH$_2$Ph), 7.20 (s, 5H, aromatic).

EXAMPLE 12

(2S*, 3R*)-3-Benzyloxy-1,1-ethylenedioxy-2-methyl-2-(4'-methyl-4'-pentenyl)-cyclohexane A suspension of sodium hydride (10.9 g, 0.227 mol) in dimethylsulfoxide (250 ml) is heated to 70° C. under a nitrogen atmosphere and stirred for 45 minutes. The mixture is cooled to 25° C. and methyltriphenylphosphonium iodide (91.7 g, 0.227 mol) in dimethylsulfoxide (100 ml) is added. The mixture is stirred for 30 minutes, (2S*, 3R*)-3-benzyloxy-1,1-ethylenedioxy-2-methyl-2-(4'-oxopentyl)-cyclohexane (15.7 g, 0.045 mol) in dimethylsulfoxide (50 ml) is added and the mixture is heated to 60° C. After 4 hours, the reaction mixture is cooled and added to saturated sodium chloride (1000 ml) and extracted with ether (5×200 ml). The ether layers are combined, dried (MgSO$_4$) and the solvent is removed under reduced pressure. The crude product (24.1 g) is chromatographed on SilicAR CC-7 (300 g, Mallinckrodt) in hexane. Elution with 4% ethyl acetate/hexane gives (2S*, 3R*)-3-benzyloxy-1,1-ethylenedioxy-2-methyl-2-(4'-methyl-4'-pentenyl)-cyclohexane as a light yellow oil (14.3 g, 92%): ir (neat) 1638 cm$^{-1}$ (C=C), nmr (CDCl$_3$)δ 1.06 (s, 3H, CH$_3$), 3.40 (m, 1H, —CH—OCH$_2$Ph), 4.50 (d of d, J=10 Hz, 2H, —O—CH$_2$Ph), 4.61 (broad s, 2H, —C=CH$_2$), 7.30 (s, 5H, aromatic).

EXAMPLE 13

(2S*, 3R*)-3-Benzyloxy-1,1-ethylenedioxy-2-methyl-2-(4'-methyl-5'-hydroxypentyl)-cyclohexane To a solution of 9-borabicyclononane (10.1 g, 0.083 mol) in tetrahydrofuran (600 ml) at 0° C. is added a solution of (2S*, 3R*)-3-benzyloxy-1,1-ethylenedioxy-2-methyl-2-(4'-methyl-4'-pentenyl)-cyclohexane (14.3 g, 0.0416 mol) in tetrahydrofuran (150 ml). The cooling bath is removed and the reaction mixture stirred for 3 hours at 25° C. The reaction mixture is decomposed at 0° C. by adding 3 N sodium hydroxide (33 ml, 0.105 mol) followed by 30% hydrogen peroxide (47.6 g, 0.42 mol). The mixture is poured into saturated sodium chloride (1000 ml) and extracted with ether (5×300 ml). The extracts are combined, dried (MgSO$_4$) and the solvent is removed under reduced pressure. The crude product (20.1 g) is chromatographed on SilicAR CC-7 (250 g, Mallinckrodt) in hexane. Elution with 8% ethyl acetate/hexane gives (2S*, 3R*)-3-benzyloxy-1,1-ethylenedioxy-2-methyl-2-(4'-methyl-5'-hydroxypentyl)-cyclohexane as a clear colorless oil (13.9 g, 91%): nmr (CDCl₃)δ0.86 (d, J=6 Hz, 3H, —CH—C$\underline{H}$₃), 1.08 (s, 3H, C$\underline{H}$₃), 3.42 (broad d, 3H, HO—C$\underline{H}$₂—CH— and O$\underline{H}$), 3.98 (s, 4H, ketal), 4.52 (d of d, 2H, Ph—C$\underline{H}$₂—O—), 7.20 (s, 5H, aromatic).

EXAMPLE 14

(2S*, 3R*)-3-Benzyloxy-2-methyl-2-(4'-methyl-5'-hydroxypentyl)-cyclohexanone

A mixture of (2S*, 3R*)-3-benzyloxy-1,1-ethylenedioxy-2-methyl-2-(4'-methyl-5'-hydroxypentyl)-cyclohexane (13.9 g, 0.0384 mol), acetone (150 ml), water (20 ml) and 0.002 N sulfuric acid (50 ml) is refluxed for 18 hours under a nitrogen atmosphere. The reaction mixture is cooled, the acetone evaporated under reduced pressure and the aqueous layer extracted with ether (3×500 ml). The combined organic layers are washed with saturated sodium bicarbonate (100 ml), saturated sodium chloride (2×200 ml) and dried (MgSO₄). The solvents are removed to afford (2S*, 3R*)-3-benzyloxy-2-methyl-2-(4'-methyl-5'-hydroxypentyl)-cyclohexanone (crude product, 12.2 g, 100%): ir (neat) 3484 (OH), 1709 cm⁻¹ (CO); nmr (CDCl₃)δ 0.88 (d, J=6 Hz, 3H, —CH—C$\underline{H}$₃), 1.08 (s, 3H, C$\underline{H}$₃), 3.42 (m, 4H, HO—C$\underline{H}$₂—CH—, O$\underline{H}$ and —C$\underline{H}$—O—CH₂Ph), 4.50 (d of d, J=10 Hz, 2H, Ph—C$\underline{H}$₂—O—), 7.2 (s, 5H, aromatic).

EXAMPLE 15

(2S*, 3R*)-3-Benzyloxy-2-methyl-2-[4'-methyl-5'-(tetrahydropyran-2''-yloxy)-pentyl]-cyclohexanone A mixture of the alcohol (2S*, 3R*)-3-benzyloxy-2-methyl-2-(4'-methyl-5'-hydroxypentyl)-cyclohexanone (12.2 g, 0.038 mol), dihydropyran (4.8 g, 0.057 mole) and p-toluenesulfonic acid (100 mg) in anhydrous ether (150 ml) is stirred at 24° C. under a nitrogen atmosphere for 18 hours. The mixture is then diluted with ether (500 ml), washed with sodium bicarbonate, water and saturated sodium chloride, dried (MgSO₄) and evaporated in vacuo to give 14.3 g of a yellow oil. The oil is chromatographed on SilicAR CC-7 (220 g, Mallinckrodt) in hexane. Elution with 5-10% ethyl acetate/hexane gives (2S*, 3R*)-3-benzyloxy-2-methyl-2-[4'-methyl-5'-(tetrahydropyran-2''-yloxy)-pentyl]-cyclohexanone as a colorless oil (14.3 g, 88%): nmr (CDCl₃)δ 0.82 (d, J=6 Hz, 3H, —CH—C$\underline{H}$₃), 1.10 (s, 3H, C$\underline{H}$₃), 4.40 (d of d, J=10 Hz, 2H, —O—C$\underline{H}$₂Ph), 4.49 (broad s, 1H, —O—C$\underline{H}$—CO—), 7.20 (s, 5H, aromatic).

EXAMPLE 16

(2S*, 3R*)-3-Benzyloxy-2-methyl-2-[4'-methyl-5'-(tetrahydropyran-2''-yloxy)-pentyl]-1-oxacycloheptan-7-one A solution of (2S, 3R*)-3-benzyloxy-2-methyl-2-[4'-methyl-5'-(tetrahydropyran-2''-yloxy)-pentyl]-cyclohexanone (7.6 g, 0.0189 mol), sodium acetate (1.64 g, 0.02 mol), m-chloroperoxybenzoic acid 85% (4.97 g, 0.0246 mole) and distilled methylene chloride (300 ml) is heated at reflux under a nitrogen atmosphere for 17 hours. The solution is cooled and filtered and the filtrate is washed with saturated sodium bicarbonate, saturated sodium chloride and dried (MgSO₄). The solvent is removed under reduced pressure and the crude product (8.2 g) chromatographed on SilicAR CC-7 (150 g, Mallinckrodt) in hexane. Elution with 10% ethyl acetate/hexane gives recovered (2S*, 3R*)-3-benzyloxy-2-methyl-2-[4'-methyl-5'-(tetrahydropyran-2''-yloxy)-pentyl]-cyclohexanone (2.8 g) while 15% ethyl acetate/hexane gives the desired lactone (2S*, 3R*)-3-benzyloxy-2-methyl-2-[4'-methyl-5'-(tetrahydropyran-2''-yloxy)-pentyl]-1-oxacycloheptan-7-one (3.5 g, 70% based on the recovery of the starting ketone): nmr (CDCl₃)δ 0.95 (d, J=6 Hz, 3H, —CH—C$\underline{H}$₃), 1.42 (s, 3H C$\underline{H}$₃), 2.62 (m, 2H, —O—CO—C$\underline{H}$₂—CH₂—), 4.60 (d of d, J=10 Hz, 2H, —O—C$\underline{H}$₂Ph), 7.22 (s, 5H, aromatic).

EXAMPLE 17

(2S*, 3R*)-Diethyl-[3-benzyloxy-2-methyl-2-(4'-methyl-5'-(tetrahydropyran-2''-yloxy)-pentyl)-3(H), 4,5-dihydro oxepinyl]-7-phosphate To a lithium diisopropylamide solution [prepared from n-butyllithium in hexane (18.2 ml, 0.0285 mol) and diisopropylamine (2.88 g, 0.0285 mol)] in dry tetrahydrofuran (100 ml) with hexamethylphosphoramide (5.1 g, 0.0285 mol) cooled to −78° C. is added dropwise a solution of (2S*, 3R*)-3-benzyloxy-2-methyl-2-[4'-methyl-5'-(tetrahydropyran-2''-yloxy)-pentyl]-1-oxacycloheptan-7-one (7.9 g, 0.019 mol) in dry tetrahydrofuran (50 ml). After stirring for 45 minutes, tetramethylethylenediamine (50 ml) is added followed by diethylchlorophosphate (4.92 g, 0.0285 mol) in tetrahydrofuran (50 ml). The cooling bath is removed and stirring at room temperature is maintained for 0.5 hours. The reaction mixture is poured into pH 7 buffer (250 ml) and extracted with ether (5×100 ml). The ether phases are combined, dried (MgSO₄) and the solvent removed under reduced pressure. The crude product (15.3 g) is chromatographed on SilicAr CC-7 (200 g, Mallinckrodt) in hexane. Elution with 20% ethyl acetate/hexane gives (2S*, 3R*)-diethyl-[3-benzyloxy-2-methyl-2-(4'-methyl-5'-(tetrahydropyran-2''-yloxy)-pentyl)-3(H), 4,5-dihydro oxepinyl]-7-phosphate as a clear light yellow oil (8.92 g, 85%): nmr (CDCl₃)δ 1.00 (d, J=6 Hz, 3H, —CH—C$\underline{H}$₃), 1.20 (s, 3H, C$\underline{H}$₃),

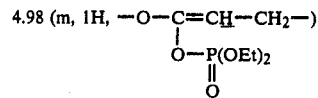

4.98 (m, 1H, —O—C=C$\underline{H}$—CH₂—)

7.30 (s, 5H, aromatic).

EXAMPLE 18

(2S*, 3R*)-3-Hydroxy-2-methyl-2-[4'-methyl-5'-(tetrahydropyran-2''-yloxy)-pentyl]-6-oxepene To a freshly distilled solution of ammonia (450 ml) cooled to −78° C. is added in an argon atmosphere t-butyl alcohol (21.4 g, 0.29 mol). The cooling bath is removed and (2S*, 3R*)-diethyl-[3-benzyloxy-2-methyl-2-(4'-methyl-5'-(tetrahydropyran-2''-yloxy)-pentyl)-3(H), 4,5-dihydro oxepinyl]-7-phosphate (8.92 g, 0.0161 mol) in tetrahydrofuran (112 ml) is added. Freshly cut sodium metal (2.22 g, 0.0966 mol) is added in small pieces at −33° C. The resulting blue solution is stirred for 0.5 hours and quenched by adding ether (450 ml) followed by water (100 ml). The ammonia is evaporated at room temperature and the mixture is poured into pH 7 buffer (1000 ml) and ether (250 ml). The ether layer is separated and the water phase is extracted with ether (5×100 ml). The ether phases are combined, washed with saturated sodium chloride (500 ml), dried (MgSO4) and the solvent is removed under reduced pressure. The crude product (5.2 g) is chromatographed on SilicAR CC-7 (75 g, Mallinckrodt) in hexane. Elution with 10% ethyl acetate/hexane gives (2S*, 3R*)-3-hydroxy-2-methyl-2-[4'-methyl-5'-(tetrahydropyran-2''-yloxy)-pentyl]-6-oxepene as a clear light yellow oil (2.7 g, 54%): ir (neat) 3481 (OH), 1650 cm$^{-1}$ (O—C=C), nmr (CDCl3)δ 0.93 (d, J=6 Hz, 3H, —CH—CH3), 1.22 (s, 3H, CH3), 4.78 (broad s, —O—CH—O—), 4.92 (m, 1H, —O—CH=CH—), 6.01 (m, 1H, —O—CH=CH—).

EXAMPLE 19

(2S*, 3R*)-3-Benzyloxy-2-methyl-2-[4'-methyl-5'-(tetrahydropyran-2''-yloxy)-pentyl]-6-oxepene To a suspension of sodium hydride (830 mg, 0.0173 mol) in benzene (50 ml) is added (2S*, 3R*)-3-hydroxy-2-methyl-2-[4'-methyl-5'-(tetrahydropyran-2''-yloxy)-pentyl]-6-oxepene (2.7 g, 0.00865 mol) in benzene (25 ml) in a nitrogen atmosphere. After 0.5 hours, benzyl bromide (3.0 g, 0.0173 mol) in benzene (25 ml) is added. The mixture is refluxed for 16 hours, cooled and poured into saturated sodium chloride (200 ml). The aqueous layer is extracted with ether (5×75 ml). The organic phases are combined, dried (MgSO4) and the solvents are removed under reduced pressure. The crude product (3.6 g) is chromatographed on SilicAR CC-7 (75 g, Mallinckrodt) in hexane. Elution with 7% ethyl acetate/hexane gives (2S*, 3R*)-3-benzyloxy-2-methyl-2-[4'-methyl-5'-(tetrahydropyran-2''-yloxy)-pentyl]-6-oxepene as a clear colorless oil (3.25 g, 93%): nmr (CDCl3)δ 0.92 (d, J=6 Hz, 3H, —CH—CH3), 1.20 (s, 3H, CH3), 4.54 (d of d, J=10 Hz, 3H, —O—CH2Ph, —O—CH—O—), 4.94 (m, 1H, —O—CH=CH—), 6.00 (d, J=6 Hz, 1H, —O—CH=CH—), 7.25 (s, 5H, aromatic).

EXAMPLE 20

(2S*, 3R*)-3-Benzyloxy-2-methyl-2-[4'-methyl-5'-(tetrahydropyran-2''-yloxy)-pentyl]-oxepan-6-ol To a solution of (2S*, 3R*)-3-benzyloxy-2-methyl-2-[4'-methyl-5'-(tetrahydropyran-2''-yloxy)-pentyl]-6-oxepane (3.25 g, 0.0081 mol) in tetrahydrofuran (60 ml) at 0° C. in a nitrogen atmosphere is added diborane (10.8 ml, 0.0108 mol, 1 M solution in tetrahydrofuran). The cooling bath is removed and the mixture is stirred for 2 hours at 25° C. The reaction mixture is then quenched by adding 3 N sodium hydroxide (5.4 ml, 0.021 mol) followed by 30% hydrogen peroxide (3.8 g, 3.6 ml, 0.111 mol). The reaction mixture is stirred at 25° C. for 1.5 hours, then poured into saturated sodium chloride (250 ml) and ether (150 ml). The ether layer is separated and the aqueous phase is extracted with ether (7×75 ml). The ether phases are combined, dried (MgSO4) and the solvents are removed at reduced pressure. Th crude product (4.1 g) is chromatographed on SilicAR CC-7 (50 g, Mallinckrodt) in hexane. Elution with 25% ethyl acetate/hexane gives (2S*, 3R*)-3-benzyloxy-2-methyl-2-[4'-methyl-5'-(tetrahydropyran-2''-yloxy)-pentyl]-oxepan-6-ol as a clear colorless oil (2.4 g, 71%): ir (neat) 3500 cm$^{-1}$ (OH): nmr (CDCl3)δ 0.92 (d, J=6 Hz, 3H, —CH—CH3), 7.25 (s, 5H, aromatic); the compound is a mixture of epimeric alcohols as shown by thin layer chromatography, ethyl acetate/hexane (40:60).

EXAMPLE 21

(2S*, 3R*)-3-Benzyloxy-2-methyl-2-[4'-methyl-5'-(tetrahydropyran-2''-yloxy)-pentyl]-oxepan-6-one A solution of pyridine (5.4 g, 0.0686 mol) and chromium trioxide (3.4 g, 0.0343 mol) in methylene chloride (150 ml) at 23° C. in a nitrogen atmosphere is stirred for 45 minutes. The mixture is cooled to −10° C. and celite (20 g) is added followed by (2S*, 3R*)-3-benzyloxy-2-methyl-2-[4'-methyl-5'-(tetrahydropyran-2''-yloxy)-pentyl]-oxepan-6-ol (2.4 g, 0.0057 mol) in methylene chloride (50 ml). After stirring for 2 hours at 0° C., the mixture is filtered and the celite cake is washed with methylene chloride (10×50 ml). The filtrate and the washings are combined and washed with saturated sodium bicarbonate (2×100 ml), dried (MgSO4) and evaporated in vacuo. The crude product (2.8 g) is chromatographed on SilicAR CC-7 (40 g, Mallinckrodt) in hexane. Elution with 10% ethyl acetate/hexane gives (2S*, 3R*)-3-benzyloxy-2-methyl-2-[4'-methyl-5'-(tetrahydropyran-2''-yloxy)-pentyl]-oxepan-6-one as a clear colorless oil (2.1 g, 88%): nmr (CDCl3)δ 1.00 (d, J=6 Hz, 3H, —CH—CH3), 1.30 (s, 3H, CH3), 2.60 (m, 2H, —CO—CH2— CH2—), 3.98 (m, 2H, —O—CH2—CO—), 4.50 (d of d, J=10 Hz, 2H, —O—CH2Ph), 4.60 (broad s, 1H, —O—CH—O—), 7.2 (s, 5H, aromatic).

EXAMPLE 22

(2S*, 3R*)-3-Benzyloxy-6,6-ethylenedioxy-2-methyl-2-(4'-methyl-5'-hydroxypentyl)-oxepane A mixture of the ketone (2S*, 3R*)-3-benzyloxy-2-methyl-2-[4'-methyl-5'-(tetrahydropyran-2''-yloxy)-pentyl]-oxepan-6-one (2.1 g, 0.005 mol), ethylene glycol (10 ml) and p-toluenesulfonic acid (350 mg) in benzene (75 ml) is refluxed for 20 hours using a Dean-Stark apparatus. The cooled solution is diluted with water (150 ml) and ether (150 ml). The organic layer is separated and the aqueous layer is extracted with ether (2×250 ml). The combined organic layers are washed with saturated sodium bicarbonate (2×50 ml), saturated sodium chloride and dried (MgSO4). The solvents are removed at reduced pressure and the crude product (2.7 g) is chromatographed on SilicAR CC-7 (50 g, Mallinckrodt) in hexane. Elution with 30% ethyl acetate/hexane gives (2S*, 3R*)-3-benzyloxy-6,6-ethylenedioxy-2-methyl-2-(4'-methyl-5'-hydroxypentyl)-oxepane as a clear colorless oil (1.5 g, 87%): ir (neat) 3450 cm$^{-1}$ (OH), nmr (CDCl3)δ 0.95 (d, J=6 Hz, 3H, —CH—CH3), 1.18 (s, 3H, CH3), 3.40

(m, 5H, OH—CH2—CH2), —CH2—CH—OCH2Ph and

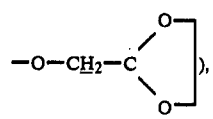

4.50 (d of d, J=10 Hz, 2H, —O—CH2Ph), 7.30 (s, 5H, aromatic).

EXAMPLE 23

(2S*, 3R*)-3-Benzyloxy-6,6-ethylenedioxy-2-methyl-2-(4'-methyl-5'-oxopentyl)-oxepane A solution of pyridine (3.6 g, 0.0444 mol) and chromium trioxide (2.2 g, 0.0222 mol) in methylene chloride (450 ml) at 23° C. in a nitrogen atmosphere is stirred for 45 minutes. The mixture is cooled to −10° C. and celite (13 g) is added followed by (2S*, 3R*)-3-benzyloxy-6,6-ethylenedioxy-2-methyl-2-(4'-methyl-5'-(hydroxypentyl)-oxepane (1.4 g, 0.0037 mol) in methylene chloride (150 ml). The mixture is stirred for 1 hour at −10° C. and 30 minutes at 0° C. The mixture is then filtered and the celite cake is washed with methylene chloride (10×50 ml). The filtrate and washings are combined and washed with saturated sodium bicarbonate (2×150 ml). The methylene chloride phase is separated, dried (MgSO₄) and the solvents are removed at reduced pressure. The crude product (1.3 g) is chromatographed on SilicAR CC-7 (25 g, Mallinckrodt) in hexane. Elution with 7–10% ethyl acetate/hexane gives (2S*, 3R*)-3-benzyloxy-6,6-ethylenedioxy-2-methyl-2-(4'-methyl-5'-oxopentyl)-oxepane as a clear colorless oil (1.157 g, 83%).

EXAMPLE 24

(2S*, 3R*)-3-Benzyloxy-6,6-ethylenedioxy-2-methyl-2-(4',8'-dimethyl-5'-hydroxy-8'-nonenyl)-oxepane A solution of 4-bromo-2-methyl-1-butene (0.760 g, 0.0051 mol) in anhydrous tetrahydrofuran (8 ml) is added dropwise over 2 hours to a suspension of Mg turnings (126 mg, 0.0052 mol) in anhydrous tetrahydrofuran (10 ml). After stirring for 1 hour, the solution is cooled to −5° to −10° C. and a solution of (2S*, 3R*)-3-benzyloxy-6,6-ethylenedioxy-2-methyl-2-(4'-methyl-5'-oxopentyl)-oxepane (1.157 g, 0.0031 mol) is added dropwise over a period of 30 minutes. The mixture is allowed to warm to 24° C. and stirred for 30 minutes; quenched with water (5 ml), poured into saturated sodium chloride and extracted with ether (5×200 ml). The organic layers are combined, dried (MgSO₄) and evaporated in vacuo to give 1.4 g of a viscous light yellow oil. The oil is chromatographed on SilicAR CC-7 (30 g, Millinckrodt) in hexane. Elution with 7–10% ethyl acetate/hexane gives (2S*, 3R*)-3-benzyloxy-6,6-ethylenedioxy-2-methyl-2-(4',8'-dimethyl-5'-hydroxy-8'-nonenyl)-oxepane as a colorless oil (1.32 g, 96%): ir (neat) 3400 cm⁻¹ (OH).

EXAMPLE 25

(2S*, 3R*)-3-Benzyloxy-6,6-ethylenedioxy-2-methyl-2-(5'-acetoxy-4',8'-dimethyl-8'-nonenyl)-oxepane A solution of the alcohol (2S*, 3R*)-3-benzyloxy-6,6-ethylenedioxy-2-methyl-2-(4',8'-dimethyl-5'-hydroxy-8'-nonenyl)-oxepane (1.32 g, 0.0029 mol) in pyridine (10 ml) and acetic anhydride (2.7 ml) is stirred under nitrogen at 24° C. for 24 hours. The reaction mixture is poured into water and stirred for 1.5 hours. The suspension is extracted with ether (5×100 ml) and the ether extracts washed with water, saturated sodium bicarbonate, water and saturated sodium chloride, dried (MgSO₄) and evaporated in vacuo to give 1.5 g of a viscous yellow oil. The oil is chromatographed on SilicAR CC-7 (30 g, Mallinckrodt) in hexane. Elution with 5–8% ethyl acetate/hexane gives (2S*, 3R*)-3-benzyloxy-6,6-ethylenedioxy-2-methyl-2-(5'-acetoxy-4',8'-dimethyl-8'-nonenyl)-oxepane (1.4 g, 97%): nmr (CDCl₃)δ 0.88 (d, J=6, 3H, —CH—C$\underline{H}$₃), 1.18 (s, 3H, C$\underline{H}$₃), 2.02 (s, 3H, OA̱c), 3.42

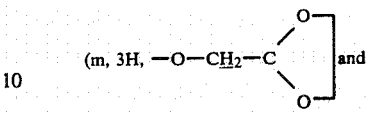

3.98 (s, 4H, ketal), 4.51 (d of d, J=10 Hz, 2H, —O—CH₂—Ph), 4.68 (broad singlet, 2H, —C=C$\underline{H}$₂), 7.25 (s, 5H, aromatic).

EXAMPLE 26

(2S*, 3R*)-3-Benzyloxy-6,6-ethylenedioxy-2-methyl-2-(5'-acetoxy-4',8'-dimethyl-7'-nonenyl)-oxepane A solution of (2S*, 3R*)-3-benzyloxy-6,6-ethylenedioxy-2-methyl-2-(5'-acetoxy-4',8'-dimethyl-8'-nonenyl)-oxepane (1.4 g, 0.0028 mol) and p-toluenesulfonic acid (200 mg) in anhydrous benzene (100 ml) is refluxed for 18 hours under a nitrogen atmosphere. The mixture is cooled to room temperature, diluted with ether (350 ml), washed with saturated sodium bicarbonate, water, saturated sodium chloride, dried (MgSO₄) and evaporated in vacuo to give (2S*, 3R*)-3-benzyloxy-6,6-ethylenedioxy-2-methyl-2-(5'-acetoxy-4',8'-dimethyl-7'-nonenyl)-oxepane (1.4 g, 100%) as a viscous light yellow oil: ir (neat) 1714 cm⁻¹ (OAc); nmr (CDCl₃)δ 0.88 (d, J=6, 3H, —CH—C$\underline{H}$₃), 1.18 (s, 3H, C$\underline{H}$₃), 2.01 (s, 3H, OA̱c), 3.41

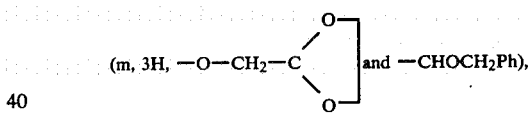

3.98 (s, 4H, ketal), 4.51 (d of d, J=10 Hz, 2H, —O—CH₂Ph), 4.94

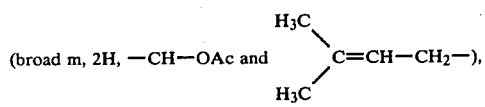

7.21 (s, 5H, aromatic).

EXAMPLE 27

(2S*, 3R*)-3-Benzyloxy-6,6-ethylenedioxy-2-methyl-2-(4',8'-dimethyl-5'-hydroxy-7'-nonenyl)-oxepane A solution of (2S*, 3R*)-3-benzyloxy-6,6-ethylenedioxy-2-methyl-2-(5'-acetoxy-4',8'-dimethyl-7'-nonenyl)-oxepane (14 g, 0.00086 mol) and saturated potassium carbonate (5 ml) in methanol (30 ml) and water (10 ml) is refluxed for 4 hours. The mixture is cooled to room temperature and the methanol is evaporated under reduced pressure. The aqueous layer is extracted with ether (5×100 ml), washed with water, saturated sodium chloride, dried (MgSO₄), and evaporated in vacuo to give (2S*, 3R*)-3-benzyloxy-6,6-ethylenedioxy-2-methyl-2-(4',8'-dimethyl-5'-hydroxy-7'-nonenyl)-oxepane as a viscous yellow oil (1.2 g, 94%).

EXAMPLE 28

(2S*, 3R*)-3-Benzyloxy-6,6-ethylenedioxy-2-methyl-2-[4',8'-dimethyl-5'-(tetrahydropyran-2''-yloxy)-7'-nonenyl]-oxepane A mixture of the alcohol (2S*, 3R*)-3-benzyloxy-6,6-ethylenedioxy-2-methyl-2-(4',8'-dimethyl-5'-hydroxy-7'-nonenyl)-oxepane (1.2 g, 0.0027 mol), dihydropyran (435 mg, 0.0054 mol) and p-toluenesulfonic acid (150 mg) in anhydrous ether (15 ml) is stirred at 24° C. under a nitrogen atmosphere for 18 hours. The mixture is diluted with ether (100 ml), washed with saturated sodium bicarbonate (2×75 ml), water, saturated sodium chloride, dried (MgSO₄) and evaporated in vacuo to give 1.3 g of a yellow oil. The oil is chromatographed on SilicAR CC-7 (25 g, Mallinckrodt) in hexane. Elution with 4% ethyl acetate/hexane gives (2S*, 3R*)-3-benzyloxy-6,6-ethylenedioxy-2-methyl-2-[4',8'-dimethyl-5'-(tetrahydropyran-2''-yloxy)-7'-nonenyl]-oxepane (1.20 g, 84%): nmr (CDCl₃) δ1.20 (s, 3H, C$\underline{H}$₃), 3.54

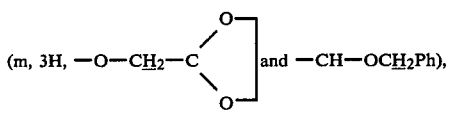

3.98 (s, 4H, ketal), 4.53 (d of d, J=10 Hz, 2H, —O—C$\underline{H}$₂Ph), 4.64 (broad m, 1H, —O—C$\underline{H}$—O—), 5.01

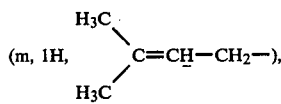

7.23 (s, 5H, aromatic).

EXAMPLE 29

(2S*, 3R*)-6,6-Ethylenedioxy-3-hydroxy-2-methyl-2-[4',8'-dimethyl-5'-(tetrahydropyran-2''-yloxy)-7'-nonenyl]-oxepane t-Butyl alcohol (1 g, 0.0135 mol) is added to a freshly distilled solution of ammonia (60 ml) cooled to −78° C. in an argon atmosphere. The cooling bath is removed and (2S*, 3R*)-3-benzyloxy-6,6-ethylenedioxy-2-methyl-2-[4',8'-dimethyl-5'-(tetrahydropyran-2''-yloxy)-7'-nonenyl]-oxepane (1.2 g, 0.0022 mol) in tetrahydrofuran (15 ml) is added. Freshly cut sodium metal (1.04 g, 0.0045 mol) is added in small pieces at −33° C. The resulting blue solution is stirred for 0.5 hours and quenched by adding ether (60 ml) followed by water (50 ml). The ammonia is evaporated at room temperature and the ether layer is separated. The water phase is extracted with ether (5×50 ml). The ether phases are combined, washed with saturated sodium chloride, dried (MgSO₄) and the solvent is removed under reduced pressure. The crude product (1.0 g) is chromatographed on SilicAR CC-7 (20 g, Mallinckrodt). Elution with 10% ethyl acetate/hexane gives (2S*, 3R*)-6,6-ethylenedioxy-3-hydroxy-2-methyl-2-[4',8'-dimethyl-5'-(tetrahydropyran-2''-yloxy)-7'-nonenyl]-oxepane as a clear colorless oil (850 mg, 86%): ir (neat) 3400 cm⁻¹ (OH); nmr (CDCl₃) δ0.78 (d, J=6 Hz, 3H, —CH—C$\underline{H}$₃), 0.82 (d, J=6 Hz, 3H, —CH—C$\underline{H}$₃), 1.20 (s, 3H, C$\underline{H}$₃), 3.38

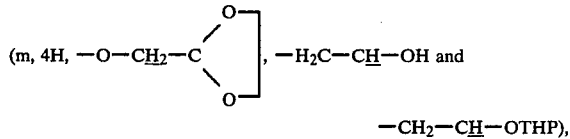

3.98 (s, 4H, ketal), 4.56 (broad s, 1H, —O—C$\underline{H}$—O—), 5.02

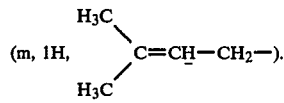

EXAMPLE 30

(2S*, 3R*)-3-Acetoxy-6,6-ethylenedioxy-2-methyl-2-[4',8'-dimethyl-5'-(tetrahydropyran-2''-yloxy)-7'-nonenyl]-oxepane A solution of (2S*, 3R*)-6,6-ethylenedioxy-3-hydroxy-2-methyl-2-[4',8'-dimethyl-5'-(tetrahydropyran-2''-yloxy)-7'-nonenyl]-oxepane (850 mg, 0.00193 mol) in pyridine (10 ml) and acetic anhydride (2.0 g) is stirred under nitrogen at 24° C. for 18 hours. The reaction mixture is then poured into water and stirred for 1.5 hours. The suspension is extracted with ether (5×50 ml) and the ether extracts are washed with water, and saturated sodium chloride, dried (MgSO₄) and evaporated in vacuo to give (2S*, 3R*)-3-acetoxy-6,6-ethylenedioxy-2-methyl-2-[4',8'-dimethyl-5'-(tetrahydropyran-2''-yloxy)-7'-nonenyl]-oxepane (800 mg, 86%): nmr (CDCl₃) δ0.80 (d, J=6 Hz, 3H, —CH—C$\underline{H}$₃), 0.85 (d, J=6 Hz, 3H, —CH—C$\underline{H}$₃), 1.18 (s, 3H, —C$\underline{H}$₃), 2.02 (s, 3H, OA$\underline{c}$), 3.42

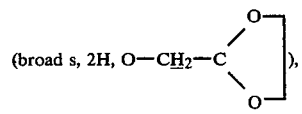

3.98 (s, 4H, ketal), 4.6 (broad s, 1H, —O—C$\underline{H}$—O—), 5.01

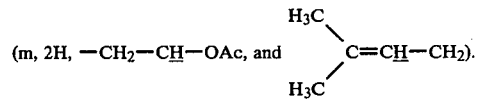

EXAMPLE 31

(2S*, 3R*)-3-Acetoxy-2-methyl-2-(4',8'-dimethyl-5'-hydroxy-7'-nonenyl)oxepan-6-one A mixture of (2S*, 3R*)-3-acetoxy-6,6-ethylenedioxy-2-methyl-2-[4',8'-dimethyl-5'(tetrahydropyran-2''-yloxy)-7'-nonenyl]-oxepane (800 mg, 0.00166 mol), acetone (20 ml), water (3.5 ml) and 0.002 N sulfuric acid (11 ml) is refluxed for 24 hours under a nitrogen atmosphere. The reaction mixture is cooled to room temperature, the acetone is evaporated under reduced pressure and the aqueous layer is extracted with ether (5×50 ml). The combined organic layers are washed with saturated sodium bicarbonate, saturated sodium chloride and dried (MgSO₄). The solvents are removed under reduced pressure and the crude product (520 mg) is chromatographed on SilicAR CC-7 (10 g, Mallinckrodt) in hexane. Elution with 10–15% ethyl acetate/hexane gives (2S*, 3R*)-3-acetoxy-2-methyl-2-(4',8'-dimethyl-5'-hydroxy-7'-nonenyl)oxepan-6-one as a colorless oil (420 mg, 71%): ir (neat) 3424 (OH), 1718 cm⁻¹ (CO and OAc); nmr (CDCl₃) δ0.82 (d, J=6 Hz, 3H, —CH—C$\underline{H}$₃), 1.18 (s, 3H, C$\underline{H}$₃), 2.00 (s, 3H, OA$\underline{c}$), 2.5 (m, 2H, —CO—C$\underline{H}$₂—CH₂—), 3.99 (s, 2H, —O—C$\underline{H}$₂—CO—), 4.91 (m, 1H, —CH₂—C$\underline{H}$—OAc), 5.10

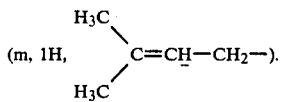

EXAMPLE 32

(2S*, 3R*)-3-Acetoxy-2-methyl-2-[4',8'-dimethyl-5'-(tetrahydropyran-2''-yloxy)-7'-nonenyl]-oxepan-6-one A mixture of (2S*, 3R*)-3-acetoxy-2-methyl-2-(4',8'-dimethyl-5'-hydroxy-7'-nonenyl)-oxepan-6-one (1.1 g), dihydropyran (500 mg) and p-toluenesulfonic acid (150 mg) in anhydrous ether (15 ml) is stirred at 24° C. under a nitrogen atmosphere for 18 hours. The mixture is then diluted with ether (100 ml), washed with saturated sodium bicarbonate (2×75 ml), water, saturated sodium chloride, dried (MgSO₄) and evaporated in vacuo to give 1.5 g of a yellow oil. The oil is chromatographed on SilicAR CC-7 (15 g) in hexane. Elution with 4% ethyl acetate/hexane gives (2S*, 3R*)-3-acetoxy-2-methyl-2-[4',8'-dimethyl-5'(tetrahydropyran-2''-yloxy)-7'-nonenyl]-oxepan-6-one as a colorless oil (1.2 g, 88%): nmr (CDCl₃) δ1.1 (s, 3H, —CH₃), 2.05 (s, 3H, —COC$\underline{H}$₃), 2.62 (m, 2H, —CO—C$\underline{H}$₂—CH₂—), 4.05 (s, 2H, —O—CH₂—CO—C$\underline{H}$₂—), 4.81

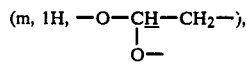

5.02

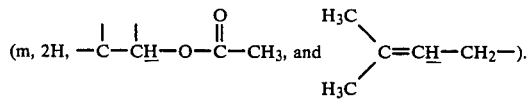

EXAMPLE 33

(2S*, 3R*)-3-Acetoxy-6-(2'-carboethoxymethylidene)-2-methyl-2-[4',8'-dimethyl-5'-(tetrahydropyran-2''-yloxy)-7'-nonenyl]-oxepane Triethyl phosphonoacetate (641 mg, 0.00285 mole) in benzene (9 ml) is added to a suspension of 99% sodium hydride (66 mg, 0.00279 mole) in benzene (1 ml). The mixture is heated to 70° C. and stirred for 2 hours. The mixture is then cooled to 25° C. and (2S*, 3R*)-3-acetoxy-2-methyl-2-[4',8'-dimethyl-5'-(tetrahydropyran-2''-yloxy)-7'-nonenyl]-oxepan-6-one (500 mg, 0.00114 mole) in benzene (10 ml) is added. The mixture is heated to 70° C. and stirred for 1 hour. The reaction mixture is then cooled to 0° C., diluted with ether (25 ml) and quenched with 5% dil HCl (20 ml). The organic layer is separated and the aqueous layer is extracted with ether (5×75 ml). The organic layers are combined, dried (MgSO₄) and evaporated to give 825 mg of a slightly yellow oil. The oil is chromatographed on silica gel (10 g, Baker) in hexane. Elution with 8% ethyl acetate/hexane gives (2S*, 3R*)-3-acetoxy-6-(2''-carboethoxymethylidene)-2-methyl-2-[4',8'-dimethyl-5'-(tetrahydropyran-2''-yloxy)-7'-nonenyl)oxepane as a colorless oil (570 mg, 98%): nmr (CDCl₃) δ0.82 (d, 3H, J=6 Hz, —CH—C$\underline{H}$₃), 1.01 (s, 3H, —C—C$\underline{H}$₃), 1.22 (t, 3H, J=6 Hz, —CH₂—C$\underline{H}$₃), 2.02 (s, 3H, —OCOC$\underline{H}$₃), 4.10 (m, 4H, J=6 Hz, —OCO—C$\underline{H}$₂CH₃ and

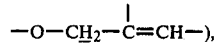

4.64

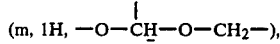

5.09

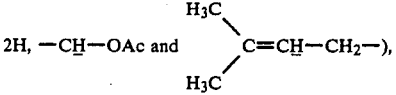

5.60 (broad s, 1H, —C═C$\underline{H}$—COOEt).

EXAMPLE 34

(2S*, 3R*)-6Z-(2''-Hydroxyethylidene)-2-methyl-2-[4',8'-dimethyl-5'-(tetrahydropyran-2''-yloxy)-7'-nonenyl]-oxepan-3-ol and (2S*, 3R*)-6E-(2''-Hydroxyethylidene)-2-methyl-2-[4',8'-dimethyl-5'-(tetrahydropyran-2''-yloxy)-7'-nonenyl]-oxepan-3-ol A solution of (2S*, 3R*)-3-acetoxy-6-(2''-carboethoxymethylidene)-2-methyl-2-[4',8'-dimethyl-5'-(tetrahydropyran-2''-yloxy)-7'-nonenyl]-oxepane (0.675 g, 0.00122 mole) in ether (8 ml) is added dropwise to a suspension of lithium aluminum hydride (0.205 g, 0.00532 mole) in ether (25 ml) at 0° C. under nitrogen. The mixture is stirred at 0° C. for 1 hour. The quenching of the reaction is accomplished by the addition of wet ethyl acetate (2 ml) and wet ether (8 ml). The mixture is diluted with saturated ammonium chloride solution and extracted with ether (5×50 ml). The ether phases are combined, dried (MgSO₄) and evaporated to give a slightly yellow oil (0.650 g). The material is chromatographed on silica gel (16 g, Baker) in hexane. Elution with 22% to 24% ethyl acetate/hexane gives (2S*, 3R*)-6Z-(2''-hydroxyethylidene)-2-methyl-2-[4',8'-dimethyl-5'-(tetrahydropyran-2''-yloxy)-7'-nonenyl]-oxepan-3-ol (155 mg), nmr (CDCl₃) δ0.85 (d, 3H, J=6 Hz, —CH—C$\underline{H}$₃), 1.18 (s, 3H, CH₃), 2.2 (m, 4H,

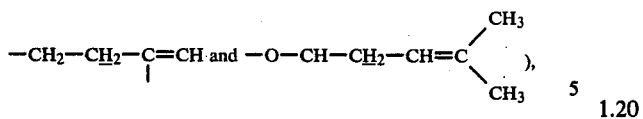

4.2

(m, 4H, —O—C<u>H</u>₂—CH—C=CH, and —C=CH—C<u>H</u>₂OH), 4.68 (broad s, 1H, —CH—O—C<u>H</u>—O—), 5.32

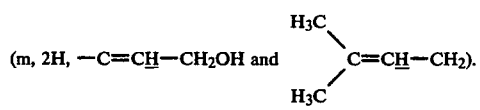

Further elution with 24% to 26% ethyl acetate gives (2S*, 2R*)-6E-(2″-hydroxyethylidene)-2-methyl-2-[4′,8′-dimethyl-5′-(tetrahydropyran-2″-yloxy)-7′-nonenyl]-oxepan-3-ol (222 mg), nmr (CDCl₃) δ0.9 (d, 3H, J=6 Hz, —CH—C<u>H</u>₃), 1.15 (s, 3H, C<u>H</u>₃), 4.18

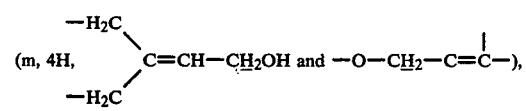

4.65

(broad s, 1H, —CH—O—C<u>H</u>—O—), 5.30

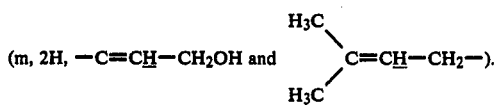

EXAMPLE 35

(2S*, 3R*)-3-Acetoxy-6Z-(2″-acetoxyethylidene)-2-methyl-2-[4′,8′-dimethyl-5′-(tetrahydropyran-2″-yloxy)-7′-nonenyl]-oxepane A solution of (2S*, 3R*)-6Z-(2″-hydroxyethylidene)-2-methyl-2-[4′,8′-dimethyl-5′-(tetrahydropyran-2″-yloxy)-7′-nonenyl]-oxepan-3-ol (0.172 g, 0.00040 mole) in pyridine (2 ml) and acetic anhydride (0.2 ml) is stirred under nitrogen at 24° C. for 18 hours. The reaction mixture is then poured into water and stirred for 1.5 hours. The suspension is extracted with ether (5×50 ml) and the ether extracts washed with water, saturated copper sulfate solution, dried (MgSO₄) and evaporated in vacuo to give 170 mg of a yellowish oil. The oil is chromatographed on silica gel (2 g, Baker) in hexane. Elution with 10% ethyl acetate/hexane gives (2S*,3R*)-3-acetoxy-6Z-(2″-acetoxyethylidene)-2-methyl-2-[4′,8′-dimethyl-5′-(tetrahydropyran-2″-yloxy)-7′-nonenyl]-oxepane (166 mg, 82%): nmr (CDCl₃) δ0.9

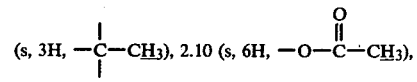

1.20

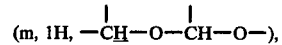

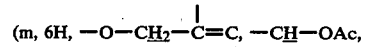

3.40

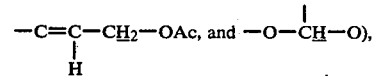

centered at 4.42

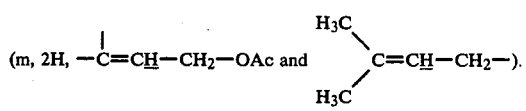

5.20

(m, 2H, —C=C<u>H</u>—CH₂—OAc and H₃C\C=C<u>H</u>—CH₂—). / H₃C

EXAMPLE 36

(2S*, 3R*)-3-Acetoxy-6Z-(2″-acetoxyethylidene)-2-methyl-2-[4′,8′-dimethyl-5′-hydroxy-7′-nonenyl]-oxepane A solution of (2S*, 3R*)-3-acetoxy-6Z-(2″-acetoxyethylidene)-2-methyl-2-[4′,8′-dimethyl-5′-(tetrahydropyran-2″-yloxy)-7′-nonenyl]-oxepane (80 mg, 0.000157 moles) in acetic acid/water/tetrahydrofuran 20:10:1 (3 ml) is stirred under nitrogen at 40° C. for 4 hours. The reaction mixture is cooled and poured into ether (50 ml) and the ether washed with saturated bicarbonate (50 ml). The ether phase is separated and the aqueous phase is extracted with ether (3×25 ml). The ether phases are combined and dried (MgSO₄). The solvents are removed under reduced pressure and the crude product (72 mg) is chromatographed on silica gel (1.1 g, Baker) in hexane. Elution with 8% ethyl acetate/hexane gives (2S*, 3R*)-3-acetoxy-6Z-(2″-acetoxyethylidene)-2-methyl-2-[4′,8′-dimethyl-5′-hydroxy-7′-nonenyl)-oxepane (61 mg, 90%): ir (neat) 3400 (OH), 1724 cm⁻¹ (OAc); nmr (CDCl₃) δ0.90 (d, J=6 Hz, 3H, —CH—C<u>H</u>₃), 1.22 (s, 3H, —C—C<u>H</u>₃), 2.06

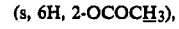

3.4

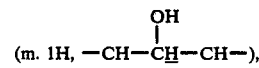

4.3

(s, 2H, —O—CH₂—C̲=CH—), 4.5 (d, 2H, —C=CH—CH₂—OAc), 4.7

(m, 1H, —CH₂—CH̲—OAc), 5.30 (m, 2H,

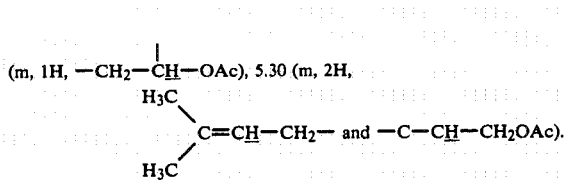

C=CH̲—CH₂— and —C—CH̲—CH₂OAc).

EXAMPLE 37

(2S*, 3R*)-3-Acetoxy-6Z-(2″-acetoxyethylidene)-2-methyl-2-[4′,8′-dimethyl-7′-nonenyl-5′-oxo]-oxepane A pyridine-chromium trioxide solution [pyridine (345 mg, 0.00385 mole) and chromium trioxide (192 mg, 0.00192 mole)] is prepared in dry methylene chloride (27 ml) at 0° C. in a nitrogen atmosphere. The cooling bath is removed and celite (1.5 g) is added at 10° C. The solution is cooled to 0° C. and (2S*, 3R*)-3-acetoxy-6Z-(2″-acetoxyethylidene)-2-methyl-2-[4′,8′-dimethyl-5′-hydroxy-7′-nonenyl]-oxepane (136 mg, 0.00032 mole) is added. After 1 hour, the mixture is filtered and the celite cake is washed with methylene chloride (10×10 ml). The organic phases are combined, washed with saturated sodium bicarbonate (2×25 ml), saturated sodium chloride and dried (MgSO₄). The solvent is removed at reduced pressure and the resulting crude product (140 mg) is chromatographed on silica gel (1.5 g, Baker) in hexane. Elution with 8% ethyl acetate/hexane gives a colorless oil (2S*, 3R*)-3-acetoxy-6Z-(2″-acetoxyethylidene)-2-methyl-2-[4′,8′-dimethyl-7′-nonenyl-5′-oxo]-oxepane (100 mg, 84%): ir (neat) 3400 (OH), 1724 cm⁻¹ (OAc); nmr (CDCl₃) δ0.90 (d, J=6 Hz, 3H, —CH—CH̲₃), 1.22 (s, 3H, —C—CH̲₃), 2.06 (s, 6H, 2—OCOCH̲₃), 3.4

(m, 1H, —CH₂—CH̲(OH)—CH), 4.3

(s, 2H, —O—CH₂—C̲=CH—), 4.5 (d, 2H, —C=CH—CH₂—OAc), 4.7

(m, 1H, —CH₂—CH̲—OAc), 5.30

(m, 2H, H₃C\C=CH̲—CH₂— and —C=CH̲—CH₂OAc).
/H₃C

EXAMPLE 38

(2S*, 3R*)-3-Acetoxy-6E-(2″-acetoxyethylidene)-2-methyl-2-[4′,8′-dimethyl-5′-(tetrahydropyran-2″-yloxy)-7′-nonenyl]-oxepane A solution of (2S*, 3R*)-6E-(2″-hydroxyethylidene)-2-methyl-2-[4′,8′-dimethyl-5′-(tetrahydropyran-2″-yloxy)-7′-nonenyl]-oxepan-3-ol (252 mg, 0.000594 mole) in pyridine (3 ml) and acetic anhydride (0.3 ml) is stirred under nitrogen at 24° C. for 18 hours. The reaction mixture is then poured into water and stirred for 1.5 hours. The suspension is extracted with ether (5×50 ml) and the ether extracts are washed with water, saturated copper sulfate solution, dried (MgSO₄) and evaporated in vacuo to give a yellowish oil (300 mg). The oil is chromatographed on silica gel (3 g, Baker) in hexane. Elution with 10% ethyl acetate/hexane gives (2S*, 3R*)-3-acetoxy-6E-(2″-acetoxyethylidene)-2-methyl-2-[4′,8′-dimethyl-5′-(tetrahydropyran-2″-yloxy)-7′-nonenyl]-oxepane (283 mg, 96%): nmr (CDCl₃) δ0.80 (d, J=6 Hz, 3H, —CH—CH̲₃), 0.90 (d, J=6 Hz, 3H, —CH—CH̲₃), 1.20

(s, 3H, —C̲—CH₃), 2.01 (s, 6H, 2—OCOCH̲₃), 4.10

(s, 2H, —O—CH₂—C̲=CH), 4.60 (m, 3H, —C=CH̲—CH₂OAc and —CH̲—OAc), 5.20

(m, 2H, —C̲=CH—CH₂OAc and H₃C\C=CH̲—CH₂—).
/H₃C

EXAMPLE 39

(2S*, 3R*)-3-Acetoxy-6E-(2″-acetoxyethylidene)-2-methyl-2-[4′,8′-dimethyl-5′-hydroxy-7′-nonenyl]-oxepane A solution of (2S*, 3R*)-3-acetoxy-6E-(2″-acetoxyethylidene)-2-methyl-2-[4′,8′-dimethyl-5′-(tetrahydropyran-2″-yloxy)-7′-nonenyl]-oxepane (280 mg, 0.00055 mole) in acetic acid/water/tetrahydrofuran 20:10:1 (5 ml) is stirred under nitrogen at 40° C. for 4 hours. The reaction mixture is cooled and poured into ether (50 ml) and the other mixture is washed with saturated sodium bicarbonate (50 ml). The ether phase is separated and the aqueous phase is extracted with ether (4×50 ml). The ether phases are combined and dried (MgSO₄). The solvents are removed under reduced pressure and the crude product (230 mg) is chromatographed on silica gel (2.3 g, Baker) in hexane. Elution with 8% ethyl acetate/hexane gives (2S*, 3R*)-3-acetoxy-6E-(2″-acetoxyethylidene)-2-methyl-2-[4′,8′-dimethyl-5′-hydroxy-7′-nonenyl]-oxepane (196 mg, 84%): nmr (CDCl₃) δ0.90 (d, J=6 Hz, 3H, —CH—CH̲₃), 1.19 (s, 3H, CH̲₃), 2.05 (s, 6H, 2—O—COCH̲₃), 3.40 (s, 1H, —CH̲—OH), 4.10

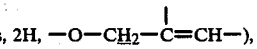 (s, 2H, —O—CH₂—C̲=CH—), 4.60 (d, 2H, —C=CH—CH₂—OAc), 4.80

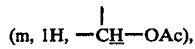 (m, 1H, —C̲H—OAc), 5.30

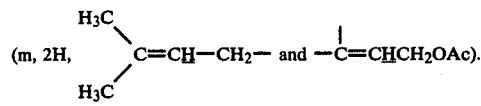 (m, 2H, (H₃C)₂C=CH—CH₂— and —C̲=C̲HCH₂OAc).

EXAMPLE 40

(2S*, 3R*)-3-Acetoxy-6E-(2″-acetoxyethylidene)-2-methyl-2-[4′,8′-dimethyl-7′-nonenyl-5′-oxo]-oxepane A solution of pyridine (440 mg, 0.00558 mole) and chromium trioxide (279 mg, 0.00279 mole) in methylene chloride (25 ml) in a nitrogen atmosphere is stirred for 45 minutes at 0° C. Celite (2 g) is added followed by (2S*, 3R*)-3-acetoxy-6E-(2″-acetoxyethylidene)-2-methyl-2-[4′,8′-dimethyl-5′-hydroxy-7′-nonenyl]-oxepane (197 mg, 0.000465 mole) in methylene chloride (25 ml). The mixture is stirred for 90 minutes at 23° C. The mixture is then filtered and the celite cake is washed with methylene chloride (10×10 ml). The filtrate and the washings are combined and the methylene chloride extracts are washed with sodium bicarbonate, water and saturated sodium chloride, dried (MgSO₄), and evaporated in vacuo. The crude product (201 mg) is chromatographed on silica gel (3 g, Baker) in hexane. Elution with 8% ethyl acetate/hexane gives (2S*, 3R*)-3-acetoxy-6E-(2″-acetoxyethylidene)-2-methyl-2-[4′,8′-dimethyl-7′-nonenyl-5′-oxo]-oxepane as a colorless oil (173 mg, 88%): ir (neat) 1710 (CO), 1740 (OAc) cm⁻¹, nmr (CDCl₃) δ1.0 (d, 3H, J=6 Hz, —CHC̲H₃), 1.18

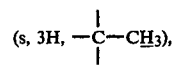 (s, 3H, —C(—C̲H₃)—), 1.62–1.78

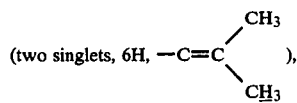 (two singlets, 6H, —C=C(CH₃)₂), 2.02

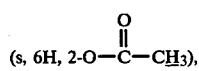 (s, 6H, 2-O—C(=O)—C̲H₃), 3.10 (s, 2H, —CO—C̲H₂—CH=C<), 4.10

 (s, 2H, —O—CH₂—C̲=CH), 4.58 (d, 2H, J=6 Hz,

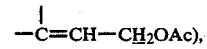 —C̲=CH—CH₂OAc), 4.80 (broad m, 1H, —C̲H—OAc), 5.15

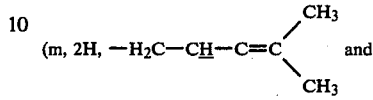 (m, 2H, —H₂C—C̲H=C(CH₃)₂ and

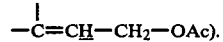 —C̲=CH—CH₂—OAc).

EXAMPLE 41

(2S*, 3R*)-6E-(2″-Hydroxyethylidene)-2-methyl-2-[4′,8′-dimethyl-5′-oxo-7′-nonenyl]-oxepan-3-ol A solution of (2S*, 3R*)-3-acetoxy-6E-(2″-acetoxyethylidene)-2-methyl-2-[4′,8′-dimethyl-7′-nonenyl-5′-oxo]-oxepane (173 mg, 0.0000410 mole), tetrabutylammonium hydroxide in methanol (40% solution, 1 ml), water (4 ml) and tetrahydrofuran (4 ml) at 25° C. in a nitrogen atmosphere is stirred for 24 hours. The solution is then diluted with saturated sodium chloride (50 ml) and the aqueous layer is extracted with ethyl acetate (5×50 ml). The combined organic layers are dried (MgSO₄) and evaporated in vacuo. The crude product (170 mg) is chromatographed on silica gel (3.5 g, Baker) in chloroform. Elution with chloroform gives (2S*, 3R*)-6E-(2″-hydroxyethylidene)-2-methyl-2-[4′,8′-dimethyl-5′-oxo-7′-nonenyl]-oxepan-3-ol as a colorless oil (110 mg, 80%): ir (neat) 3448 (OH) 1709 (CO) cm⁻¹, 5.41

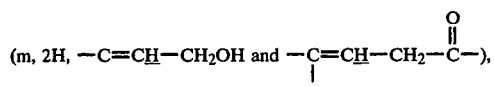 (m, 2H, —C=C̲H—CH₂OH and —C=C̲H—CH₂—C(=O)—), 4.18 (d, 2H, J=6 Hz,

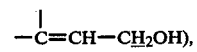 —C̲=CH—CH₂OH), 4.10

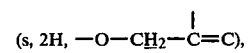 (s, 2H, —O—CH₂—C̲=C), 3.40

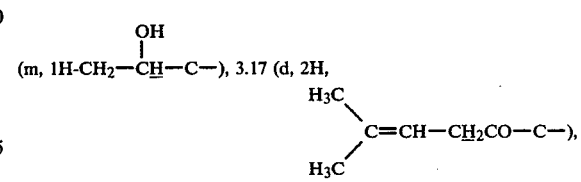 (m, 1H-CH₂—C̲H(OH)—C—), 3.17 (d, 2H, (H₃C)₂C=CH—C̲H₂CO—C—), 1.64 (d, 6H, —HC=C—(C̲H₃)₂),

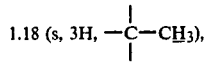

1.05 (d, J=6 Hz, 3H, —CH=C<u>H</u>₃); Mass spectrum m/e, 320 (M-18), 302 (M-2H₂O), 251, 233, 141, 125, 113, 97, 95, 81, 69.

EXAMPLE 42

(2S*, 3R*)-6Z-(2″-Hydroxyethylidene)-2-methyl-2-[4′,8′-dimethyl-5′-oxo-7′-nonenyl]-oxepan-3-ol A solution of (2S*, 3R*)-3-acetoxy-6Z-(2″-acetoxyethylidene)-2-methyl-2-[4′,8′-dimethyl-7′-nonenyl-5′-oxo]-oxepane (100 mg, 0.000236 mole), tetrabutylammonium hydroxide in methanol (40% solution, 1 ml), water (4 ml) and tetrahydrofuran (4 ml) at 25° C. in a nitrogen atmosphere is stirred for 24 hours. The solution is diluted with saturated sodium chloride (50 ml) and the aqueous layer is extracted with ethyl acetate (5×50 ml). The combined organic layers are dried (MgSO₄) and evaporated in vacuo. The crude product (210 mg) is chromatographed on silica gel (1.5 g, Baker) in chloroform. Elution with chloroform gives (2S*, 3R*)-6Z-(2″-hydroxyethylidene)-2-methyl-2-[4′,8′-dimethyl-5′-oxo-7′-nonenyl]-oxepan-3-ol as a colorless oil (65 mg, 81%): ir (neat) 3448 (OH), 1709 (CO) cm⁻¹, nmr (CDCl₃) δ5.41

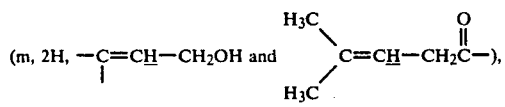

4.22

4.05 (d, 2H, J=4 Hz,

3.50 (broad t, 1H,

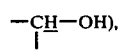

3.17

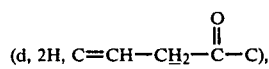

1.71 [(d, 6H, —C=C—(CH₃)₂)], 1.16

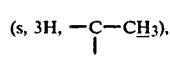

1.07 (d, 3H, J=5 Hz, —CH—C<u>H</u>₃); Mass spectrum m/e, 320 (M-18), 302 (M-2H₂O), 251, 233, 141, 125, 113, 97, 95, 81, 69.

What is claimed is:

1. The process for the preparation of a compound selected from the group consisting of

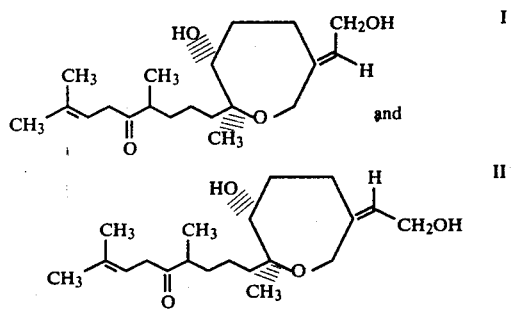

which comprises reacting a compound of the formula

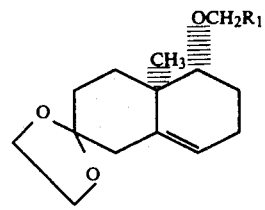

with an acid selected from p-toluenesulfonic acid, camphorsulfonic acid and oxalic acid to form a ketone of the formula

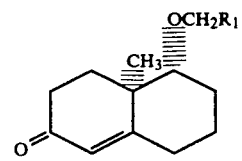

reacting the ketone with hydrogen peroxide to form an epoxide of the formula

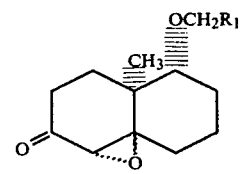

reacting the epoxide with p-toluenesulfonylhydrazide to form a compound of the formula

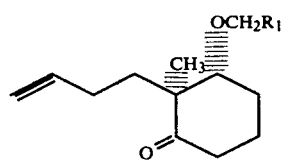

reacting the ketone formed with ethylene glycol to form a compound of the formula

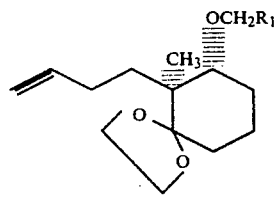

reacting the product with 9-borabicyclononane followed by reaction with hydrogen peroxide in the presence of a base selected from sodium hydroxide and potassium hydroxide to form an alcohol of the formula

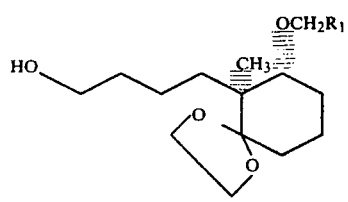

reacting the alcohol with chromium trioxide in pyridine to form an aldehyde of the formula

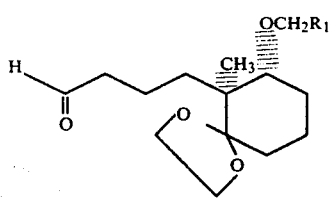

reacting the aldehyde with a compound selected from methylmagnesium bromide and methyllithium to form a compound of the formula

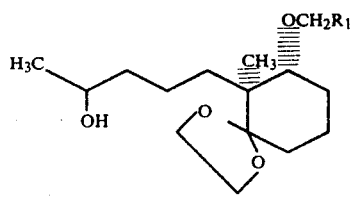

reacting the product formed with chromium trioxide-pyridine to form a ketone of the formula

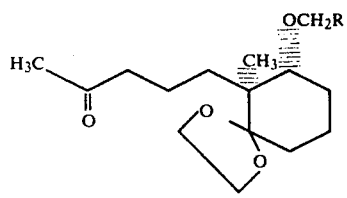

reacting the ketone with a compound selected from methyltriphenylphosphonium bromide and methyltriphenylphosphonium iodide to form a compound of the formula

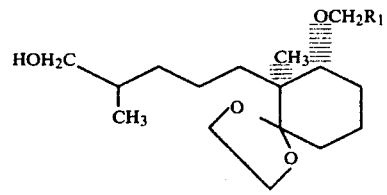

reacting the product formed with 9-borabicyclononane followed by reaction with hydrogen peroxide in the presence of a base to form an alcohol of the formula

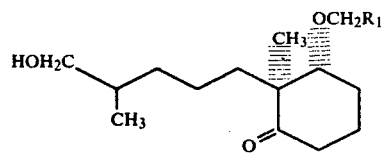

reacting the alcohol formed with an acid selected from aqueous sulfuric acid, camphorsulfonic acid and p-toluenesulfonic acid and alcoholic acetic acid to form a compound of the formula

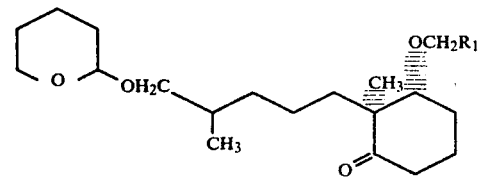

reacting the product formed with dihydropyran to form a compound of the formula

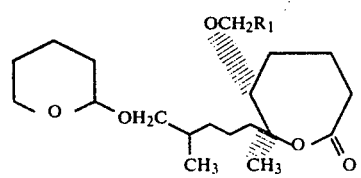

reacting the product formed with a peroxy acid selected from nitroperoxybenzoic acid and m-chloroperoxybenzoic acid to form a compound of the formula reacting the product formed first with lithium diisopropylamide and then with diethylchlorophosphate to form a compound of the formula

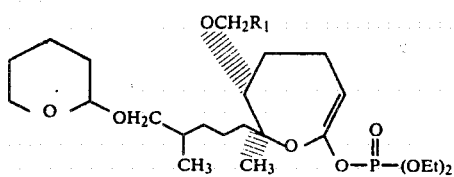

reacting the product formed with sodium in liquid ammonia to form a compound of the formula

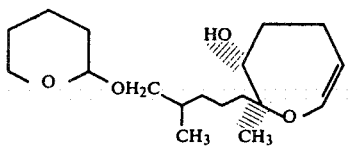

reacting the alcohol formed with a halide of the formula $R_1$-$CH_2X$ to form a compound of the formula

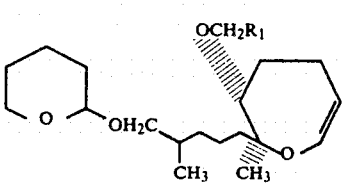

reacting the product formed with diborane followed by reaction with hydrogen peroxide in the presence of a base selected from sodium hydroxide and potassium hydroxide to form a mixture of compounds of the formula

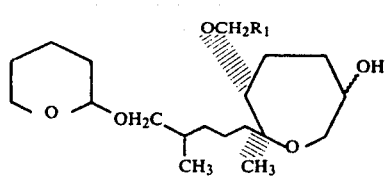

reacting the alcohols formed with chromium trioxide-pyridine to form a ketone of the formula

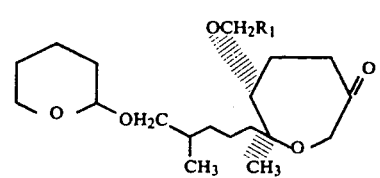

reacting the product formed with ethylene glycol in the presence p-toluenesulfonic acid to form a ketal of the formula

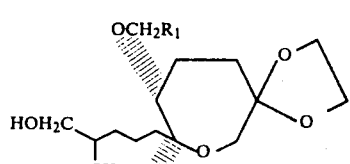

reacting the product formed with chromium trioxide-pyridine to form a compound of the formula

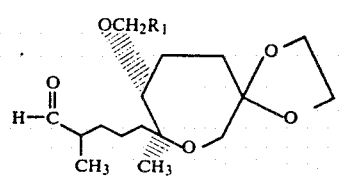

reacting the aldehyde formed with a compound of the formula

to form a compound of the formula

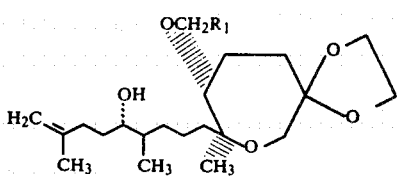

reacting the product formed with an esterifying agent selected from acetic anhydride, propionic anhydride, butyric anhydride, acetyl chloride, propionyl bromide and propionyl chloride to from an ester of the formula

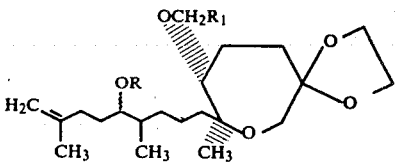

reacting the product formed with p-toluenesulfonic acid to give a compound of the formula

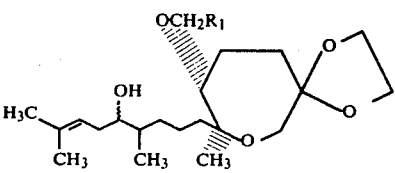

hydrolyzing the ester with a base selected from potassium carbonate and sodium carbonate to form an alcohol of the formula

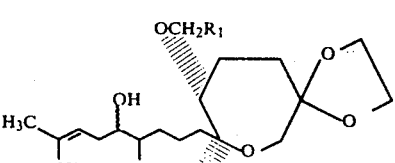

reacting the alcohol formed with dihydropyran to form a compound of the formula

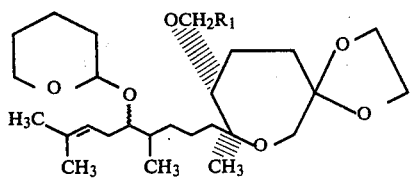

reacting the product formed with sodium in liquid ammonia to form a compound of the formula

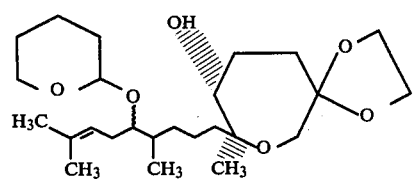

reacting the alcohol formed with an esterifying agent selected from acetic anhydride, propionic anhydride, butyric anhydride, acetyl chloride, propionyl bromide and propionyl chloride to form an ester of the formula

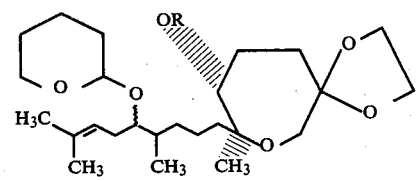

reacting the compound formed with an acid selected from acetic acid, camphor sulfonic acid and p-toluenesulfonic acid to form a ketone of the formula

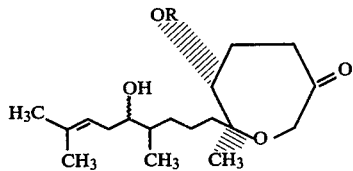

reacting the product formed with dihydropyran to form a compound of the formula

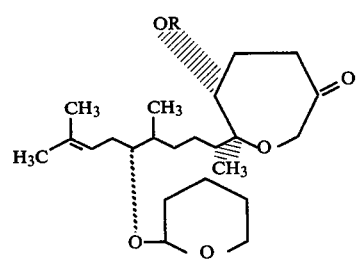

reacting the product formed with triethyl phosphonoacetate to form compounds of the formula

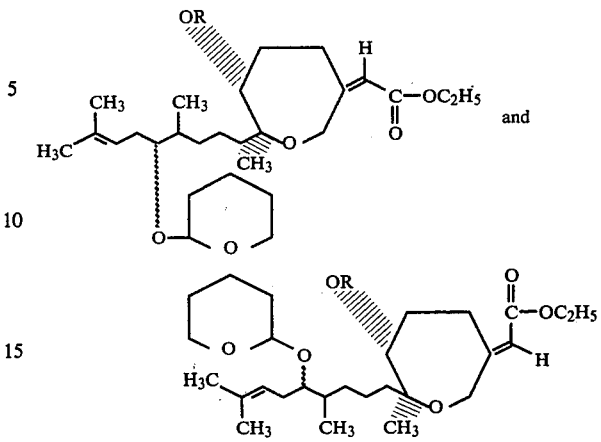

reacting the products formed with lithium aluminum hydride to form compounds of the formula

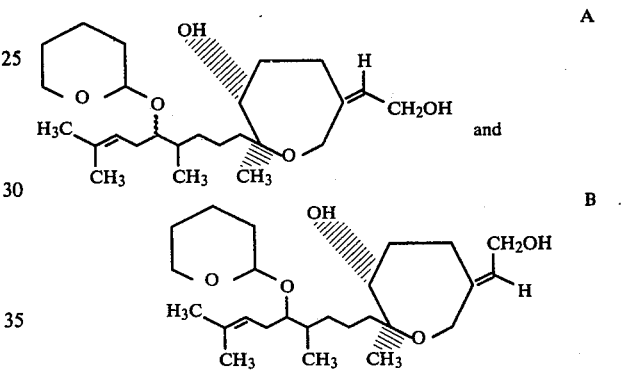

separating the compounds in the mixture, and then
(a) reacting compound A with an esterifying agent selected from acetic anhydride, propionic anhydride, butyric anhydride, acetyl chloride, propionyl bromide and propionyl chloride to form an ester of the formula

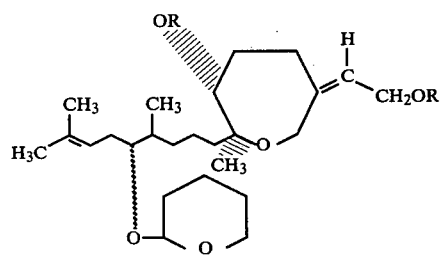

treating the ester with an organic acid selected from acetic acid, camphorsulfonic acid and p-toluenesulfonic acid to form a compound of the formula

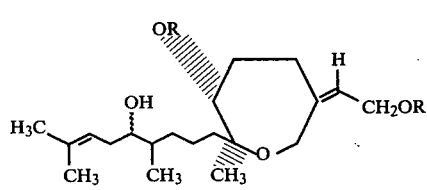

treating the alcohol formed with chromium trioxide pyridine to form a ketone of the formula

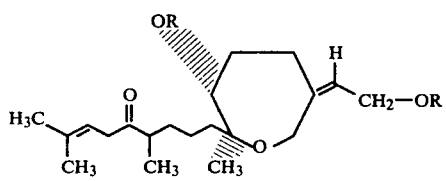

and reacting the compound formed with tetrabutylammonium hydroxide to form a compound of the formula

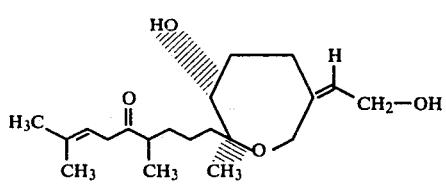

and
(b) reacting compound B with an esterifying agent selected from acetic anhydride, propionic anhydride, butyric anhydride, acetyl chloride, propionyl bromide and propionyl chloride to form an ester of the formula

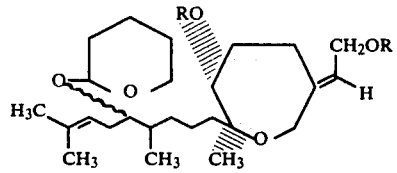

treating the ester formed with an acid selected from acetic acid, camphorsulfonic acid and p-toluenesulfonic acid to form a compound of the formula

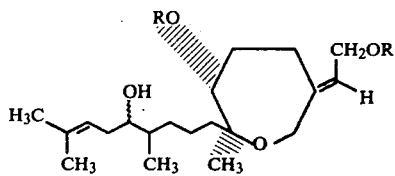

treating the alcohol formed with chromium trioxide-pyridine to form a ketone of the formula

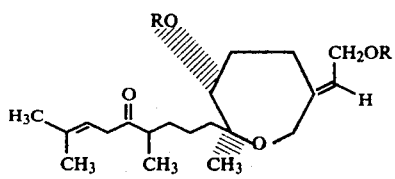

and reacting the compound formed with tetrabutylammonium hydroxide to form a compound of the formula

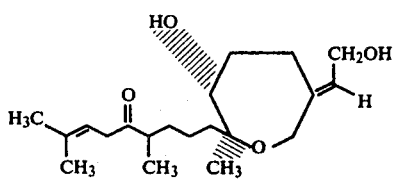

wherein R is lower alkanoyl having 2-4 carbon atoms, $R_1$ is selected from the group consisting of phenyl, p-nitrophenyl, p-methylphenyl, and X is selected from chloro, bromo and iodo.

2. The process of claim 1 wherein the esterifying agent is acetic anhydride.

3. The process of claim 1 wherein the halide is benzyl bromide and the aqueous acid is sulfuric acid.

4. The process of claim 1 wherein the organic acid is acetic acid.

* * * * *